US007512448B2

(12) United States Patent
Malick et al.

(10) Patent No.: US 7,512,448 B2
(45) Date of Patent: Mar. 31, 2009

(54) ELECTRODE PLACEMENT FOR WIRELESS INTRABODY COMMUNICATION BETWEEN COMPONENTS OF A HEARING SYSTEM

(75) Inventors: Crista Malick, Palo Alto, CA (US); Xie Qi, Champaign, IL (US); Mitesh Parikh, Elkridge, MD (US); Steve Franke, Urbana, IL (US); Douglas L. Jones, Champaign, IL (US); Jeffery B. Larsen, Charleston, IL (US); Christopher D. Schmitz, St. Joseph, IL (US); Francois Callias, Fontaines (CH)

(73) Assignee: Phonak AG, Stafa (CH)

( * ) Notice: Subject to any disclaimer, the term of this patent is extended or adjusted under 35 U.S.C. 154(b) by 1070 days.

(21) Appl. No.: 10/340,529

(22) Filed: Jan. 10, 2003

(65) Prior Publication Data

US 2004/0138723 A1 Jul. 15, 2004

(51) Int. Cl.
*A61N 1/05* (2006.01)

(52) U.S. Cl. ......................................... 607/136; 607/55

(58) Field of Classification Search ............. 607/55–57, 607/60, 136–137; 600/25, 379; 623/10; 381/330, 314–315, 68.6, 328; 181/130–135
See application file for complete search history.

(56) References Cited

U.S. PATENT DOCUMENTS

| | | | |
|---|---|---|---|
| 3,123,678 A * | 3/1964 | Prentiss et al. | 381/330 |
| 4,025,721 A | 5/1977 | Graupe et al. | |
| 4,207,441 A | 6/1980 | Ricard et al. | |
| 4,304,235 A | 12/1981 | Kaufman | |
| 4,334,740 A | 6/1982 | Wray | |
| 4,354,064 A | 10/1982 | Scott | |
| 4,536,887 A | 8/1985 | Kaneda et al. | |
| 4,559,642 A | 12/1985 | Miyaji et al. | |
| 4,611,598 A | 9/1986 | Hortmann et al. | |
| 4,703,506 A | 10/1987 | Sakamoto et al. | |
| 4,742,548 A | 5/1988 | Sessler et al. | |

(Continued)

FOREIGN PATENT DOCUMENTS

DE 28 23 798 9/1979

(Continued)

OTHER PUBLICATIONS

Capon, J., "High-Resolution Frequency-Wavenumber Spectrum Analysis", *Proceedings of the IEEE*, 57(8):1408-1419 (Aug. 1969).

(Continued)

*Primary Examiner*—Carl H Layno
*Assistant Examiner*—Brian T. Gedeon
(74) *Attorney, Agent, or Firm*—L. Scott Paynter; Krieg DeVault LLP

(57) ABSTRACT

A number of ear-worn hearing system devices are provided that each include a pair of electrodes to transmit time varying electrical signals therebetween when in contact with skin of a user's body. The devices each include a housing, a sound sensor, and processing circuitry included within the housing. The electrodes are coupled to the circuitry and are spaced apart from one another a distance sufficient to provide capacitance between the electrodes below a desired threshold. The electrodes are disposed along the housing for placement on locations of the user's body where skin contact is not likely to be disrupted by nominal body movements.

43 Claims, 13 Drawing Sheets

U.S. PATENT DOCUMENTS 4,752,961 A 6/1988 Kahn
4,773,095 A 9/1988 Zwicker et al.
4,790,019 A 12/1988 Hueber
4,845,755 A 7/1989 Busch et al.
4,858,612 A 8/1989 Stocklin
4,918,737 A 4/1990 Luethi
4,982,434 A 1/1991 Lenhardt et al.
4,987,897 A 1/1991 Funke
4,988,981 A 1/1991 Zimmerman et al.
5,000,194 A * 3/1991 van den Honert et al. ... 607/137
5,012,520 A 4/1991 Steeger
5,029,216 A 7/1991 Jhabvala et al.
5,040,156 A 8/1991 Föller
5,047,994 A 9/1991 Lenhardt et al.
5,113,859 A 5/1992 Funke
5,245,556 A 9/1993 Morgan et al.
5,259,032 A 11/1993 Perkins et al.
5,285,499 A 2/1994 Shannon et al.
5,289,544 A 2/1994 Franklin
5,321,332 A 6/1994 Toda
5,325,436 A 6/1994 Soli et al.
5,383,915 A 1/1995 Adams
5,400,409 A 3/1995 Linhard
5,417,113 A 5/1995 Hartley
5,430,690 A 7/1995 Abel
5,454,838 A 10/1995 Vallana et al.
5,463,694 A 10/1995 Bradley et al.
5,473,701 A 12/1995 Cezanne et al.
5,479,522 A 12/1995 Lindemann et al.
5,485,515 A 1/1996 Allen et al.
5,495,534 A 2/1996 Inanaga et al.
5,507,781 A 4/1996 Kroll et al.
5,511,128 A 4/1996 Lindemann
5,550,923 A 8/1996 Hotvet
5,627,799 A 5/1997 Hoshuyama
5,651,071 A 7/1997 Lindemann et al.
5,663,727 A 9/1997 Vokac
5,694,474 A 12/1997 Ngo et al.
5,706,352 A 1/1998 Engebretson et al.
5,715,319 A 2/1998 Chu
5,721,783 A 2/1998 Anderson
5,734,976 A 3/1998 Bartschi et al.
5,737,430 A 4/1998 Widrow
5,755,748 A 5/1998 Borza
5,757,932 A 5/1998 Lindemann et al.
5,768,392 A 6/1998 Graupe
5,793,875 A 8/1998 Lehr et al.
5,825,898 A 10/1998 Marash
5,831,936 A 11/1998 Zlotnick et al.
5,833,603 A 11/1998 Kovacs et al.
5,878,147 A 3/1999 Killion et al.
5,889,870 A 3/1999 Norris
5,914,701 A 6/1999 Gersheneld et al.
5,991,419 A 11/1999 Brander
6,002,776 A 12/1999 Bhadkamkar et al.
6,009,183 A * 12/1999 Taenzer et al. .............. 381/330
6,010,532 A 1/2000 Kroll et al.
6,023,514 A 2/2000 Strandberg
6,068,589 A 5/2000 Neukermans
6,094,150 A 7/2000 Ohnishi et al.
6,104,822 A 8/2000 Melanson et al.
6,118,882 A 9/2000 Haynes
6,137,889 A 10/2000 Shennib et al.
6,141,591 A 10/2000 Lenarz et al.
6,154,552 A 11/2000 Koroljow et al.
6,160,757 A 12/2000 Täger et al.
6,161,046 A 12/2000 Maniglia et al.
6,167,312 A 12/2000 Goedeke
6,173,062 B1 1/2001 Dibachi et al.
6,182,018 B1 1/2001 Tran et al.
6,192,134 B1 2/2001 White et al.
6,198,693 B1 3/2001 Marash
6,217,508 B1 4/2001 Ball et al.
6,222,927 B1 4/2001 Feng et al.
6,223,018 B1 4/2001 Fukumoto et al.
6,229,900 B1 5/2001 Leenen
6,243,471 B1 6/2001 Brandstein et al.
6,261,224 B1 7/2001 Adams et al.
6,272,229 B1 8/2001 Baekgaard
6,275,596 B1 8/2001 Fretz et al.
6,283,915 B1 9/2001 Aceti et al.
6,307,945 B1 10/2001 Hall
6,317,703 B1 11/2001 Linsker
6,327,370 B1 12/2001 Killion et al.
6,332,028 B1 12/2001 Marash
6,342,035 B1 1/2002 Kroll et al.
6,380,896 B1 4/2002 Berger et al.
6,385,323 B1 5/2002 Zoels
6,389,142 B1 5/2002 Hagen et al.
6,390,971 B1 5/2002 Adams et al.
6,397,186 B1 5/2002 Bush et al.
6,421,448 B1 7/2002 Arndt et al.
6,424,721 B1 7/2002 Hohn
6,751,325 B1 6/2004 Fischer
6,754,472 B1 * 6/2004 Williams et al. ............ 455/100
6,778,674 B1 8/2004 Panasik et al.
6,826,430 B2 * 11/2004 Faltys et al. ................ 607/137
6,861,944 B1 3/2005 Hoepelman
7,206,423 B1 * 4/2007 Feng et al. .................. 381/312
2001/0031996 A1 10/2001 Leysieffer
2001/0036284 A1 11/2001 Leber
2001/0049466 A1 12/2001 Leysieffer et al.
2001/0051776 A1 12/2001 Lenhardt
2002/0012438 A1 1/2002 Leysieffer et al.
2002/0019668 A1 2/2002 Stockert et al.
2002/0029070 A1 3/2002 Leysieffer et al.
2002/0057817 A1 5/2002 Darbut
2002/0110255 A1 8/2002 Killion et al.
2002/0131613 A1 9/2002 Jakob
2002/0141595 A1 10/2002 Jouppi
2003/0215106 A1 11/2003 Hagen et al.

FOREIGN PATENT DOCUMENTS

DE 33 22 108 A1 12/1984
DE 195 41 648 C2 5/2000
EP 0 802 699 10/1997
EP 0 824 889 2/1998
EP 0 843 425 A2 5/1998
WO WO 98/26629 6/1998
WO WO 98/56459 12/1998
WO WO 00/30404 5/2000
WO WO 01/06851 A1 2/2001
WO WO 01/39569 A2 6/2001
WO WO 01/87011 A2 11/2001
WO WO 01/87014 A2 11/2001

OTHER PUBLICATIONS

Frost, Otis Lamont III, "An Algorithm for Linearly Constrained Adaptive Array Processing", *Proceedings of the IEEE*, 60(8):926-935 (Aug. 1972).

Griffiths, Lloyd J. and Jim, Charles W., "An Alternative Approach to Linearly Constrained Adaptive Beamforming", *Transactions on Antennas and Propagation*, AP-30(1):27-34 (Jan. 1982).

Hoffman, M.W.; Trine, T.D.; Buckley, K.M. and Van Tasell, D.J. "Robust adaptive microphone array processing for hearing aids: Realistic speech enhancement", *The Journal of the Acoustical Society of America*, 96(2)(1):759-770 (Aug. 1994).

Kollmeier, Birger; Peissig, Jürgen and Hohmann, Volker, "Real-time multiband dynamic compression and noise reduction for binaural hearing aids", *Journal of Rehabilitiation Research and Development*, 30(1):82-94 (1993).

Lindemann, W., "Extension of a binaural cross-correlation model by contralateral inhibitioj. 1. Simulation of lateralization forr stationary signals", *The Journal of the Acoustical Society of America*, 80(6)1608-1622 (Dec. 1986).
Link, Michael J. and Buckley, Kevin M., "Prewhitening for intelligibility gain in hearing aid arrays", *The Journal of the Acoustical Society of America*, 93(4)(1):2139-2145 (Apr. 1993).
Peissig, Jürgen and Kollmeier, Birger, "Directivity of binaural noise reduction in spatial multiple noise-source arrangements for normal and impaired listeners", *The Journal of the Acoustical Society of America*, 101(3):1660-1670 (Mar. 1997).
Soede, Wm.; Berkhout, Augustinus J. and Bilsen, Frans A., "Development of a directional hearing instrument based on array technology", *The Journal of the Acoustical Society of America*, (94(2)(1):785-798 (Aug. 1993).
Stadler, R.W. and Rabinowitz, W.M., "On the potential of fixed arrays for hearing aids", *The Journal of the Acoustical Society of America*, 94(3)(1):1332-1342 (Sep. 1993).
Tichavsky, Petr; Wong, Kainam Thomas; and Zoltowski, Michael D., "Near-Field/Far-Field Azimuth and Elevation Angle Estimation Using a Single Vector Hydrophone", *IEEE Transactions on Signal Processing*, vol. 49, No. 11 (Nov. 2001).
Zimmerman, T.G., "Personal Area Networks: Near-field intrabody communication", *IBM Systems Journal*, 35(3,4):609-617 (1996).
T. Starner et al., Augmented Reality Through Wearable Computing, MIT Media Lab Perceptual Computing Section Technical Report No. 397, 1997, MIT Media Lab, Cambridge, MA.
E. Post et al., Intrabody Buses for Data and Power, Physics and Media, MIT Media Laboratory, Cambridge, MA, at least as early as 1997.
T.G. Zimmerman, Personal Area Networks: Near-field intrabody communication, IBM Systems Journal, 1996, MIT Media Lab, vol. 35, No. 3 & 4, pp. 609-617.
T. Zimmerman, Personal Area Networks (PAN): A Technology Demonstration by IBM Research, IBM Systems Journal, 1996, MIT Media Lab, vol. 35, No. 3 & 4.
J. Paradiso et al., Musical Applications of Electric Field Sensing, Physics and Media Group—MIT Media Laboratory, Apr. 1996, Computer Music Journal.
T.G. Zimmerman et al., Applying Electric Field Sensing to Human-Computer Interfaces, MIT Media Lab—Physics and Media Group, IEEE Sig, May 1995.

* cited by examiner

ELECTRODE PLACEMENT FOR WIRELESS INTRABODY COMMUNICATION BETWEEN COMPONENTS OF A HEARING SYSTEM

BACKGROUND OF THE INVENTION

The present invention relates to communication systems, and more particularly, but not exclusively, relates to communication between hearing system devices.

Various approaches have been suggested to communicate between electronic devices carried on a person's body. Of particular interest is the communication between components of a hearing system. Such systems frequently include a signal processor, one or more microphone units, and/or hearing stimulus units spaced apart from one another relative to a user's body. U.S. patent application Ser. No. 09/805,233 filed on Mar. 13, 2001; Ser. No. 09/568,435 filed on May 10, 2000, and Ser. No. 09/568,430 filed on May 10, 2000; and U.S. Pat. No. 6,222,927 B1 are cited as further sources concerning various hearing systems.

Interconnecting body-carried components for hearing aids and other applications with wires or cables to facilitate electrical or optical communication between the components is generally undesirable. Indeed, wireless Radio Frequency (RF) communications through the atmosphere or an earth ground have been suggested to address this shortcoming. However, communication through the transmission of signals in this manner also has certain drawbacks, such as the potential for interference by stray signals, the difficulty of incorporating needed elements into a size and form factor that can be comfortably worn by the user, and/or the likelihood of a high degree of signal attenuation. Accordingly, there is an ongoing demand for further contributions in this area of technology.

SUMMARY

One embodiment of the present invention includes a unique communication technique. Other embodiments include unique apparatus, systems, devices, and methods for communicating signals.

A further embodiment comprises a hearing system device that is configured to be worn on or in the ear of a user. The device includes a pair of electrodes disposed along the device to be placed proximate to or in contact with the user's skin. The device includes circuitry to transmit and/or receive time varying electrical signals through the person's body via the electrodes. In one form, the device is shaped to be received in the user's ear canal with the electrodes contacting skin along a top portion and a bottom portion of the canal. In another form, the device is shaped to be worn behind the ear with electrodes spaced apart from one another. In yet another form, the device is shaped to be worn behind the ear and is symmetric about a plane to facilitate interchanging it between the right and left ears.

Yet a further embodiment includes: providing a hearing system device including a first electrode and a second electrode; positioning the device in an ear canal or behind the ear of a user, placing the electrodes along corresponding skin regions; and generating a time varying electric potential between the electrodes to transmit information to another hearing system device utilizing the person as an electrical signal transmission line between the devices. When in the ear canal, the electrodes are generally disposed opposite one another to contact or be placed proximate to skin along top and bottom portions of the ear canal. For the behind-the-ear form, the electrodes are spaced apart from one another so that one is positioned along a skin region above an uppermost extreme of the concha of the ear and another is positioned along a skin region below this extreme.

Still another embodiment includes providing a housing for a hearing system device and a pair of electrodes; determining a maximum desired capacitance between the electrodes when carried by the housing and placed in contact with skin of a user; and disposing the electrodes along the housing with a separation distance, shape, and size to operate with a capacitance at or below the maximum desired capacitance and provide skin contact unbroken by normal body movements. In one form the device is of an In-The-Ear (ITE) canal type and in another form the device is of a Behind-The-Ear (BTE) type.

For a further embodiment, a hearing system device carried with the ear of a person and adapted to contact the person's skin, includes circuitry and a pair of electrodes each coupled to the circuitry. One or more of the electrodes are carried within the interior of the device and are spaced apart from one another to operate as a dipole antenna to selectively communicate information through the person as the hearing system device is carried with the ear.

Yet another embodiment includes a hearing system device with circuitry, a first member shaped to be carried behind the ear of a person, and a second member shaped to be placed in the ear canal of the person. The first member includes a first electrode to be placed in close proximity to or contact with a first skin region comprised of one or more of skin on a pinna, on a cranial region, and of a juncture between the pinna and cranial region for the ear. The second member includes a second electrode to be placed in close proximity to or contact with a second skin region along the ear canal. At least one of the first member and the second member carry the circuitry which is coupled to the first electrode and the second electrode to selectively communicate information through the person as the hearing system device is carried with the ear.

Another embodiment includes: providing a first device including a first electrode, a second electrode, a third electrode, and circuitry coupled to each of these electrodes; placing the first device in a position relative to a body of a person to put the electrodes in close proximity to or in contact with corresponding skin regions of the person; and electrically transmitting information through the body with each of a number of different pairings of the first electrode, the second electrode, and the third electrode.

In still other embodiments, multiple hearing system devices can be utilized between which one-way or two-way communication can occur via electrode pairs operating as dipole antennae. These devices can include a control device that has an interface for optional communication with an off-body unit. Alternatively or additionally, such further devices can include an implant unit. Multiple device systems can be used for intrabody communication via electrode pairs for purposes other than implementation of a hearing system. By way of nonlimiting example, such body worn devices as a headset with one or more earphones and/or one or more microphones, a Personal Digital Assistant (PDA), a mobile phone, a medical monitoring or treatment device, and the like are among those types of devices that could be used for purposes other than to enhance normal hearing or impaired hearing of a person.

One object of the present invention is to provide a unique communication technique.

Another object of the present invention is to provide a unique apparatus, system, device, or method for communicating signals.

Further objects, forms, embodiments, features, aspects, benefits, and advantages of the present invention shall become apparent from the detailed drawings and descriptions provided herein.

BRIEF DESCRIPTION OF THE DRAWING

In the following figures, like reference numerals represent like features. In some cases, the figures or selected features thereof are not drawn to scale to enhance clarity.

DETAILED DESCRIPTION OF SELECTED EMBODIMENTS

Figure 1:
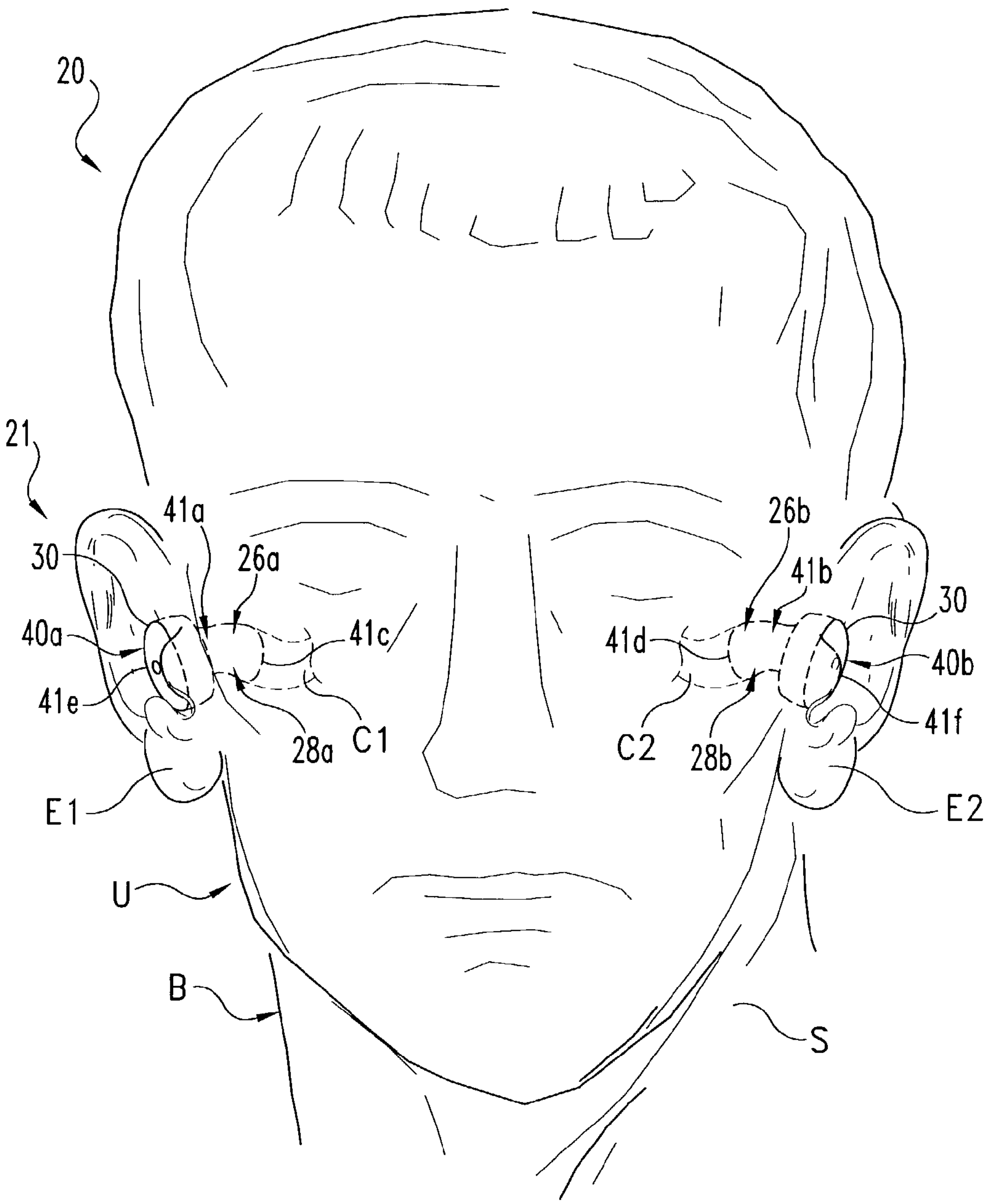
FIG. 1 is a front view of a hearing system as worn by a user, with portions of the system obscured by the user's body being shown in phantom.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present invention is directed to an intrabody communication system that utilizes the user's body as an electrical signal transmission line. In one form, this system is utilized to provide a Body Area Network (BAN) to communicate between various body-worn devices, such as a headset with one or more earphones and/or one or more microphones, a Personal Digital Assistant (PDA), a mobile phone, a medical monitoring and/or treatment unit, and the like. In another form, this system is utilized to communicate between components of a hearing system to enhance normal hearing or impaired hearing of a person.

Referring to FIG. 1, intrabody communication system 20 is illustrated, which is in the form of hearing system 21. FIG. 1 depicts an upper portion of body B of a person (user U) carrying hearing system devices 30. Body B includes ears E1 and E2 with corresponding ear canals C1 and C2 shown in phantom. Devices 30 are each at least partially placed in the ear canal C1 or C2 of ear E1 and E2, respectively; and portions of devices 30 within the ear canals C1 or C2 are shown in phantom in FIG. 1. Devices 30 are more specifically designated In-The-Ear (ITE) devices 40*a* and 40*b*. Devices 40*a* and 40*b* include respective housings 41*a* and 41*b*. Housings 41*a*, 41*b* can be provided in one or more standardized shapes and/or sizes, or can be customized through molding or another procedure to the shape and size of the ear canals of a specific person. Housings 41*a* and 41*b* are each made from an electrical insulator.

Figure 2:
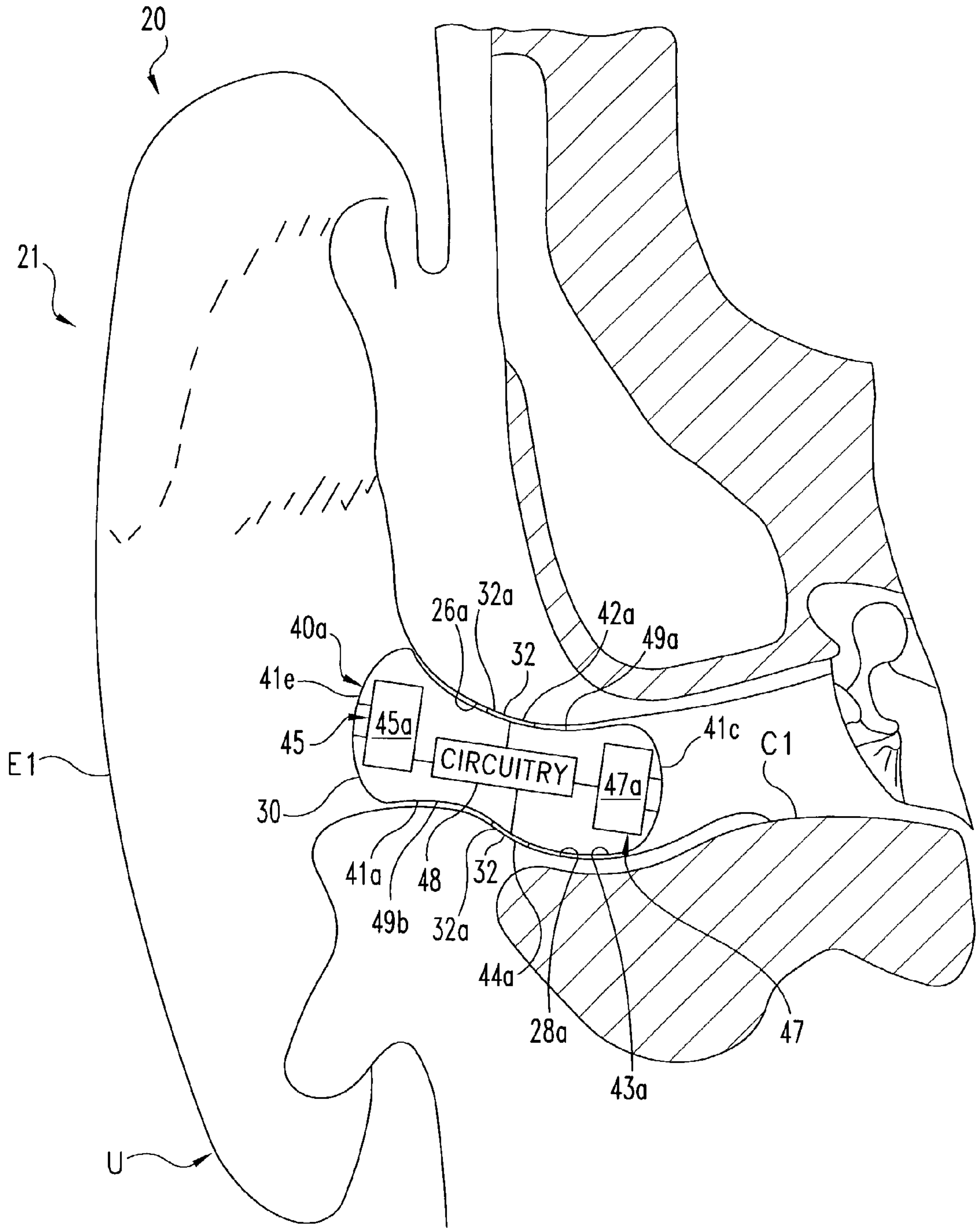
FIG. 2 is a partial schematic view illustrating further details of In-The-Ear (ITE) canal devices of FIG. 1 relative to a partial sectional view of the user's right ear.
Figure 3:
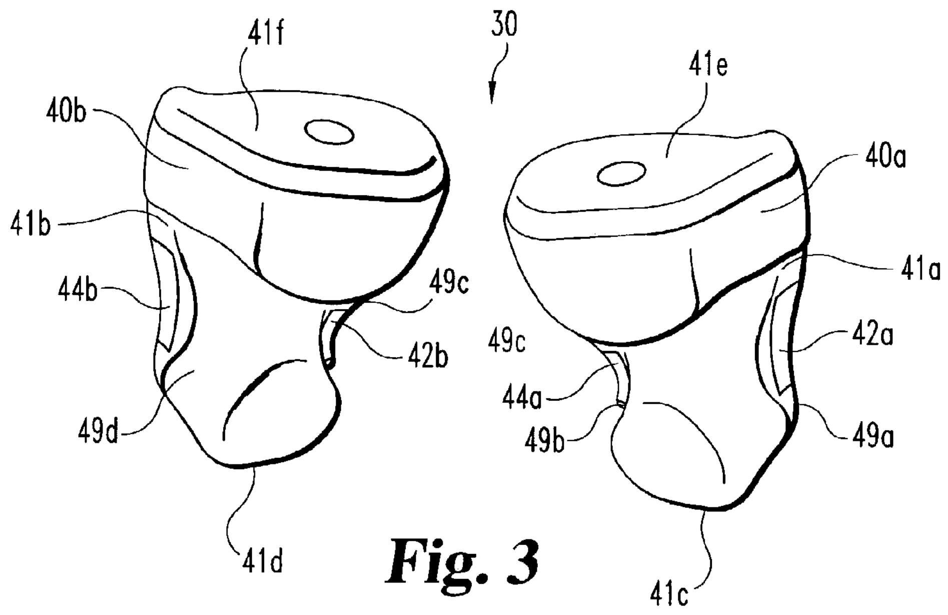
FIG. 3 is a perspective view of the ITE devices of the system of FIG. 1
Figure 4:
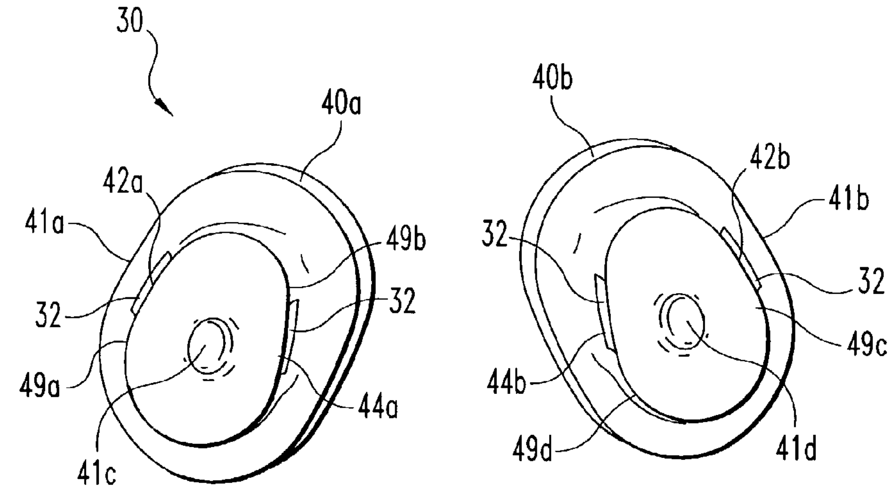
FIG. 4 is an end view of the ITE devices of the system of FIG. 1.

Referring also to FIGS. 2-4, further details concerning device 40*a* as positioned in canal C1 are shown, it being understood that device 40*b* is similarly configured, but is not depicted in FIG. 2 to enhance clarity. FIG. 2 provides a more detailed view of device 40*a* relative to the structures of ear E1 and body structures in the vicinity of ear E1. FIG. 3 presents a perspective view of devices 40*a* and 40*b*. FIG. 3 further illustrates the curvilinear contours in three dimensions of devices 40*a* and 40*b* arranged to generally conform to the approximate S-shape of ear canals C1 and C2, respectively. FIG. 4 presents an end view of housing 41*a* and 41*b*, showing end portions 41*c* and 41*d*, respectively that are positioned inside ears E1 and E2 when devices 40*a* and 40*b* are placed in the respective ear canals C1 and C2. End portions 41*c* and 41*d* are each shown with an aperture to facilitate the delivery of a hearing stimulus as is further described hereinafter. Opposite end portions 41*c* and 41*d* are corresponding end portions 41*e* and 41*f* of housings 41*a* and 41*b*, respectively. End portions 41*e* and 41*f* are visible at the exterior opening of ear canal C1 when device 40*a* is worn in a normal fashion. End portions 41*e* and 41*f* are also each shown with an aperture to facilitate reception of sound as is further described hereinafter. Housing 41*a* includes upper side portion 49*a* opposite lower side portion 49*b*, and housing 41*b* includes upper side portion 49*c* opposite lower side portion 49*d*. Side portions 49*a* and 49*b* are positioned between and joining together end portions 41*c* and 41*e*, and side portions 49*c* and 49*d* are positioned between and joining together end portions 41*d* and 41*f*.

Devices 40*a* and 40*b* each include a pair of electrodes 32 configured to contact skin S of body B along respective ear canals C1 and C2, and/or be placed in close proximity to skin S. As used herein, "close proximity" between two objects means within two (2) millimeters of one another. Electrodes 32 operate to transmit and receive signals through skin S of the body B by utilizing body B positioned between devices 40*a* and 40*b* to communicate information-containing electrical signals. For the purposes of such communications, it has been found that the performance of electrodes 32 can, as a pair, be modeled as a near-field electromagnetic signal radiator and receptor of a dipole antenna type, utilizing skin S and/or other tissues of body B as transmission media. Accordingly, each pair of electrodes 32 of devices 40*a* and 40*b* are also designated as dipole antenna 32*a* in FIG. 2. Furthermore, electrodes 32 of device 40*a* are alternatively designated antenna constituent 42*a* and antenna constituent 44*a;* and electrodes 32 of device 40*b* are alternatively designated antenna constituent 42*b* and antenna constituent 44*b.* Antenna constituent 42*a* is disposed generally opposite antenna constituent 44*a* along corresponding opposing side portions 49*a* and 49*b* of housing 41*a,* and antenna constituent 42*b* is disposed generally opposite antenna constituent 44*b* along corresponding opposing side portions 49*c* and 49*d* of housing 41*b.*

Figure 5:
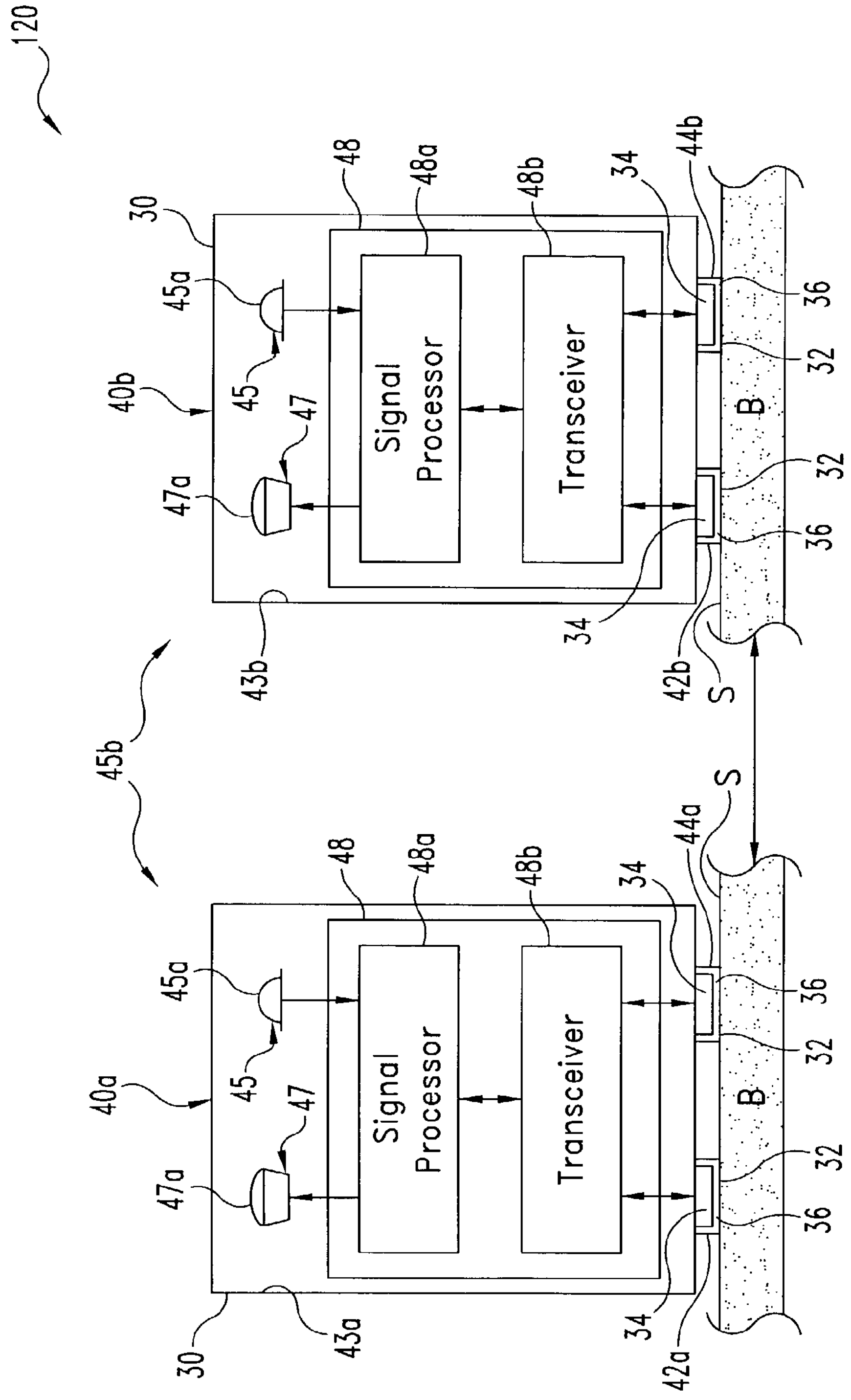
FIG. 5 is a schematic diagram of the system of FIG. 1.

As illustrated in the schematic diagram of FIG. 5, electrodes 32 include a metallic member 34 and a dielectric layer 36 covering at least a portion of member 34. Dielectric layer 36 is selected to capacitively couple the corresponding member 34 with skin S of Body B and to protect member 34 from corrosion or other deterioration due to contact with body B. In one embodiment, metallic member 34 is in the form of a 3 millimeter by 10 millimeter copper strip having a thickness of about 90 micrometers and dielectric layer 36 is in the form of a 90 micrometer thick, standard hearing aid lacquer. In another embodiment, a relatively thinner dielectric layer 36 of about 8 micrometers of Galxyl-parylene is utilized. In further embodiments, different materials, thicknesses, shapes, dimensions, and/or sizes can be utilized for member 34 and/or dielectric layer 36 as would occur to those skilled in the art. In still another example, dielectric layer 36 is absent. It should be understood that the specific shape of electrodes 32 and/or spacing between electrodes may vary with differently sized and/or shaped housings.

Referring to FIGS. 2 and 5, devices 40*a* and 40*b* each include sound sensor 45 in the form of microphone 45*a*. Microphone 45*a* can be of an omnidirectional type, or a directional type such as those with a cardioid, hypercardioid, or figure-8 directional pattern to name just a few. Each device 40*a,* 40*b* can include more than one sound sensor and/or microphone 45*a* can be of a type that includes multiple sound-detecting elements. Collectively sensors 45 of devices 40*a* and 40*b* define sensing array 45*b*. Devices 40*a* and 40*b* also each include at least one hearing stimulator 47 in the form of earphone 47*a*.

Housing 41*a* and 41*b* each define a respective cavity 43*a* and 43*b,* that each contain circuitry 48. As shown in FIG. 5, circuitry 48 includes signal processor 48*a* and transceiver 48*b* coupled together to bidirectionally communicate signals therebetween. Signal processor 48*a* is coupled to sensor 45 to receive input signals therefrom, and to stimulator 47 to provide output signals thereto. Transceiver 48*b* is coupled to electrodes 32.

Signal processor 48*a* may be comprised of one or more components of a digital type, analog type or a combination of these operable to perform desired operations as described hereinafter. Signal processor 48*a* can be of a programmable variety responsive to programming instructions stored in memory of a volatile and/or nonvolatile type, be of a dedicated hardwired logic variety, and/or execute logic defined by both dedicated hardware and program instructions. Signal processor can include only a single central processing unit or a number of processing units. For multiple processing unit embodiments, parallel and/or pipeline processing may be utilized. In one form, signal processor 48*a* is based on a customized, digital signal processor in the form of a solid-state, integrated circuit device.

As used herein, "transceiver" refers broadly to any device having a capability to transmit and receive information. Transceiver 48*b* includes a transmitter (not shown) and receiver (not shown) both coupled to electrodes 32 to transmit and receive information-containing electrical signals. These electrical signals are typically transmitted in a modulated format that conveys digital information, including but not limited to one or more of the following: Amplitude Shift Keying (ASK), a Frequency Shift Keying (FSK), Phase Shift Keying (PSK), Pulse Width Modulation (PWM), or Pulse Amplitude Modulation (PAM), Quadrature Amplitude Modulation (QAM), Orthogonal Frequency Division Multiplexing (OFDM), or spread spectrum techniques. Alternatively or additionally, an analog signal format and/or modulation technique (such as analog Amplitude Modulation (AM) or Frequency Modulation (FM)) can be utilized. The transmitter includes a drive amplifier to output an electrical signal that generates a desired electric potential level across electrodes 32 while in contact with skin S. Components of transceiver 48*b* are selected to provide a desired level of impedance matching with skin S, including, but not limited to baluns, predefined cable lengths, and/or other passive components, just to name a few.

Circuitry 48 further includes any power supplies (not shown), filters, signal conditioners, format converters (such as analog-to-digital and/or digital-to-analog converters), volatile memories, nonvolatile memories, and the like desired to perform its operations. Electrical power can be provided in the form of an electrochemical cell or battery and/or a different source as would occur to those skilled in the art.

Referring generally to FIGS. 1-5, one mode of operation of system 21 is next described. Devices 40*a* and 40*b* are positioned in ear canals C1 and C2, respectively. When so positioned, antenna constituent 42*a* of device 40*a* and antenna constituent 42*b* of device 40*b* each contact or are in close proximity to upper skin regions 26*a* and 26*b* (FIGS. 1 and 2) along a top portion of ear canals C1 and C2. Correspondingly, antenna constituent 44*a* of device 40*a* and antenna constituent 44*b* of device 40*b* each contact or are in close proximity to lower skin regions 28*a* and 28*b* (FIGS. 1 and 2) along a bottom portion of ear canals C1 and C2.

To communicate from one of devices 30 to another of devices 30, signals from signal processor 48*a* of the transmitting device 30 are encoded with the corresponding transceiver 48*b* and output as a time-varying electric potential across electrodes 32 of such device 30. The receiving device 30 detects the time-varying electrical signals with its transceiver 48*b* and decodes such signals for use by its signal processor 48*a*. The preferred range of carrier frequencies for such information-containing electrical signals is in a range of about 3 MegaHertz (MHz) through about 30 GigaHertz (GHz). A more preferred range is about 10 MHz through about 1 GHz.

This form of electrical signal communication uses skin S and/or other tissues of body B as a transmission line, such that at least two spaced apart electrodes, forming a dipole antenna, contact or are in close proximity to body B at each transmission and reception site. In contrast, other techniques have at most only one contact pathway, relying instead on a pathway through Earth ground or the atmosphere to provide an electrical potential difference necessary to provide a closed loop pathway for electrical signal communication. In FIG. 5, the bidirectional (two-way) communication of signals through body B via pairs of electrodes 32 for each of device 30 is represented by a double-headed arrow. In other embodiments, one or more of devices 30 can be configured for only one-way communication, being limited to just transmission or reception.

Consistent coupling of electrodes 32 to skin S is generally desirable because it provides for more consistent transmission characteristics of electrical signals through body B. It has been found that the anterior and posterior sides of the ear canals tend to change shape with nominal movements of the jaw, such as talking and eating, making consistent contact with electrodes 32 of devices 40*a* and 40*b* difficult. In contrast, movements of the top and bottom portions of the ear canals with nominal jaw movements are generally much less. Accordingly it has been advantageously discovered that more consistent contact between electrodes 32 and skin S within the ear canal can be achieved by placement of the electrodes 32 in a manner to contact and/or be proximate to skin S along the top and/or bottom portions of the ear canal (such as skin regions 26*a*, 26*b*, 28*a*, and 28*b*).

In another aspect, disposing antennae pairs on opposite sides of housing 41*a* and 41*b* has been found to reduce capacitance between antennae that also provides a more desirable impedance level for communications via human skin. Nonetheless, in other embodiments, one or more electrodes (antennae) may be located along skin in an anterior or posterior region along the ear canal and/or two or more electrodes (antennae) may not be positioned opposite one another. As used herein, "upper," "lower," "top," "bottom," "anterior, "posterior," "front," and "back" refer to relative positions of features of a user's body when the user's body is in an upright sitting or standing position.

Continuing with this mode of operation, once each device 40*a* and 40*b* is positioned, the corresponding sensors 45 are utilized to pick up sound which is converted into an electrical input signal that is provided to circuitry 48. The sound signals from the spaced apart sensors 45 can be utilized to selectively enhance sound originating from a particular direction relative to sounds (noise) from other directions utilizing a fixed or adaptive beamforming routine, and/or other binaural signal processing routine for a hearing aid or system as described, for example, in International Patent Applications Nos. PCT/US01/15047, PCT/US01/14945, or PCT/US99/26965; U.S. patent application Ser. Nos. 09/805,233, 09/568,435, or 09/568,430; and/or U.S. Pat. No. 6,222,927 B1. To perform such procedures, at least one of devices 40*a* and 40*b* receives sound-representative signals from sensor 45 of the other of devices 40*a* and 40*b* to generate an enhanced output signal for one of stimulators 47 to stimulate hearing of the user. To generate output signals for both stimulators 47, bidirectional communications between devices 40*a* and 40*b* are envisioned as part of the execution of routines of the type referenced hereinbefore. Further, communications between device 40*a* and 40*b* can be desired to share processing workload between the corresponding signal processors 48*a* in a distributed manner and/or to perform diagnostic or troubleshooting routines of one device 30 with another device 30. Alternatively or additionally, other processing techniques can be used to provide a desired type of hearing stimulus that utilizes one-way or two-way intrabody communication of electrical information-containing signals via electrodes 32. While devices 40*a* and 40*b* are shown as being of an In-The-Ear (ITE) type, one or more of these devices can be of a Completely-In-The-Ear-Canal (CIC) type or Behind-The-Ear (BTE) type.

Figure 6:
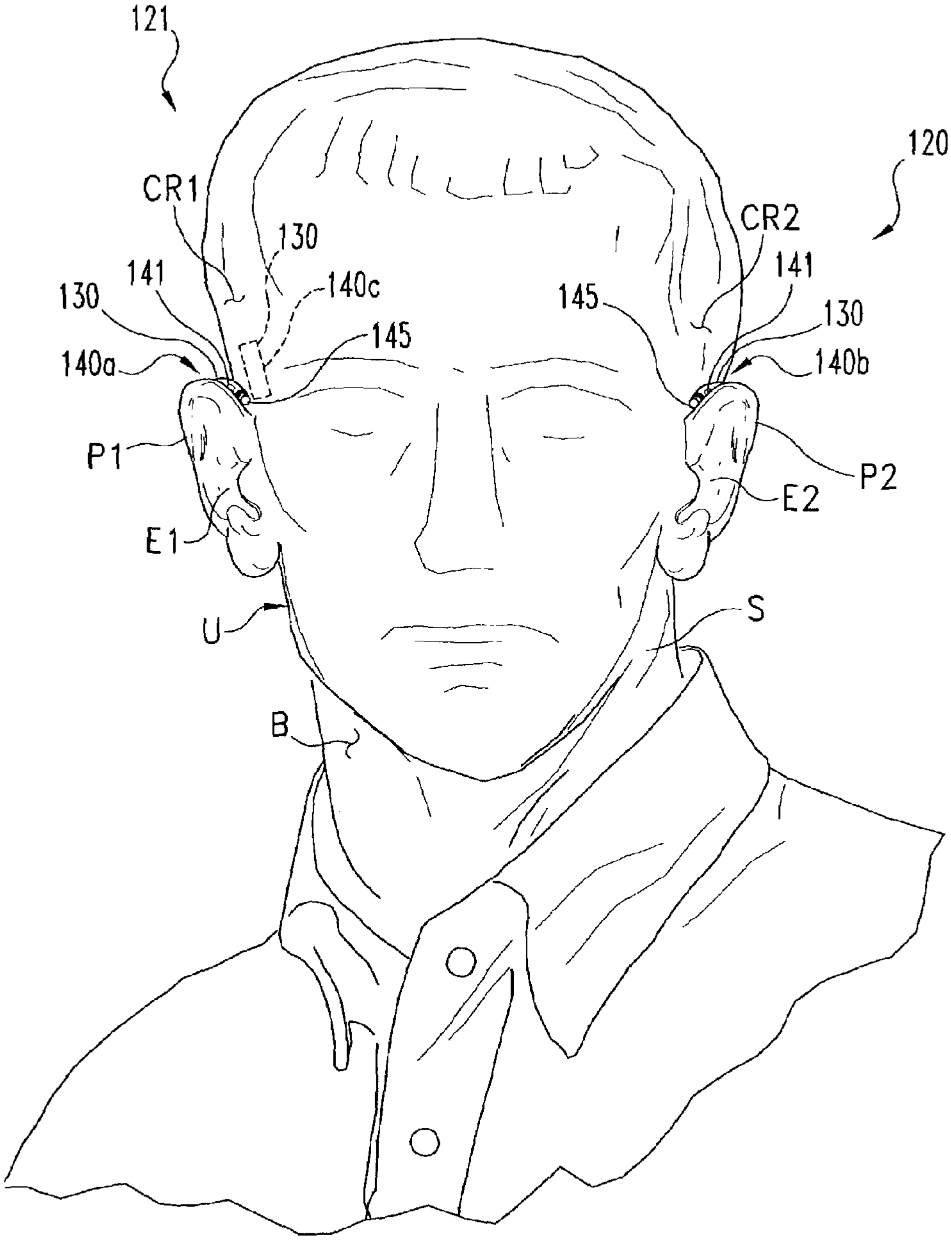
FIG. 6 is a front view of another hearing system as worn by a user, with an implant device of the system shown in phantom.

FIG. 6 illustrates another communication system 120 where like reference numerals refer to like features previously described in connection with system 20. System 120 is in the form of hearing system 121. System 121 includes three hearing system devices 130. Devices 130 are more specifically designated Behind-the-Ear (BTE) devices 140*a* and 140*b*, and implant 140*c*.

Figure 7:
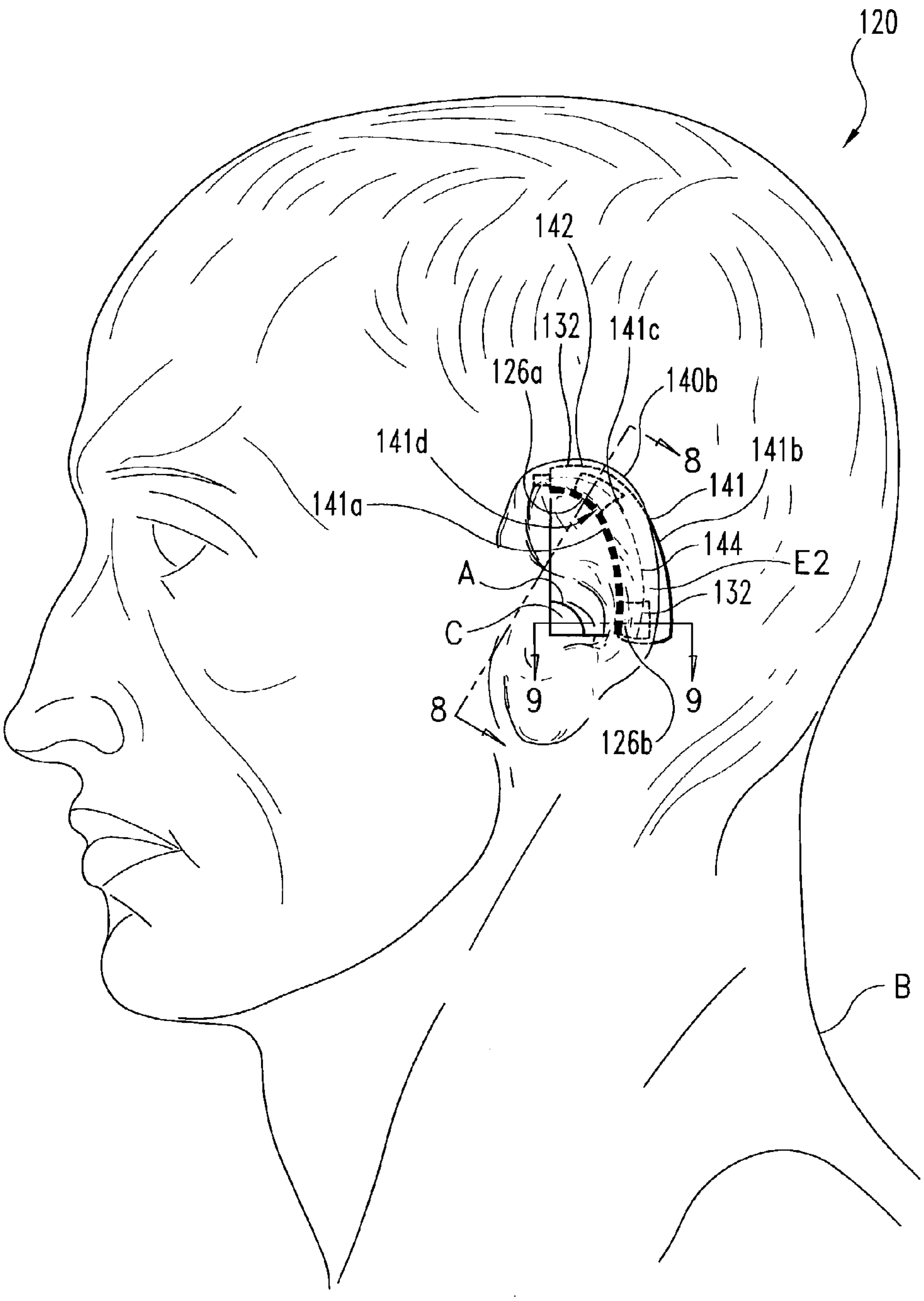
FIG. 7 is a side view of a Behind-The-Ear (BTE) device of the system of FIG. 6 relative to the user's left ear, with portions of the user's pinna of the left ear covering the BTE device shown in phantom to enhance clarity.

Referring additionally to FIGS. 7-10, devices 140*a* and 140*b* each include housing 141 and each include a pair of spaced apart electrodes 132. Housing 141 is shaped to fit behind either ear E1 and E2 of body B of system user U. When positioned behind ear El or E2, housing 141 is generally located between the corresponding pinna P1 or P2 and cranial region CR1 or CR2 of the user U, respectively. Housing 141 is made from an electrical insulator. Housing 141 includes a lower portion 141*a* opposite an upper portion 141*b* joined together by two opposing sides 141*c*. At its lowest extreme, portion 141*a* defines a lower contour 141*d*. Lower contour 141*d* is schematically indicated by a corresponding dashed line of heavier weight in FIG. 7. Lower contour 141*d* generally defines a hook-shape to facilitate behind-the-ear fitting. Lower contour 141*d* can be curvilinear, rectilinear, or a combination of both. As illustrated in FIG. 7, the hook-shape of lower contour 141*d* subtends an angle A about the corresponding pinna P2. Preferably, angle A is between about 60 and 120 degrees. More preferably, angle A is between about 75 and 105 degrees. Still more preferable, angle A is approximately 90 degrees. Nonetheless, in other embodiments, a different angle A can be utilized.

Figure 8:
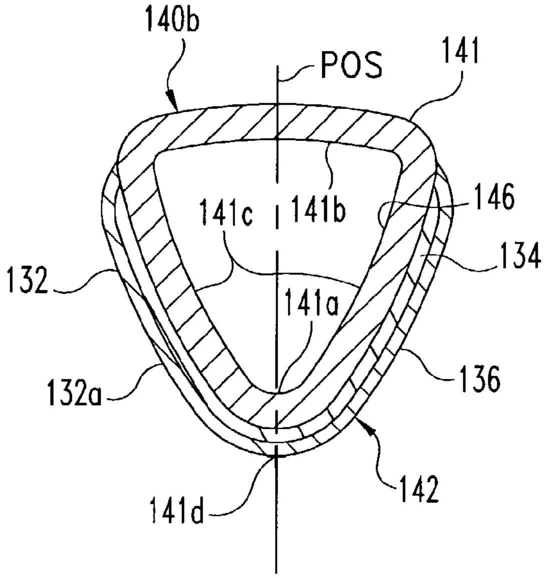
FIG. 8 is a partial, sectional view of the BTE device of FIG. 7 taken along section line 8-8 of FIG. 7.
Figure 9:
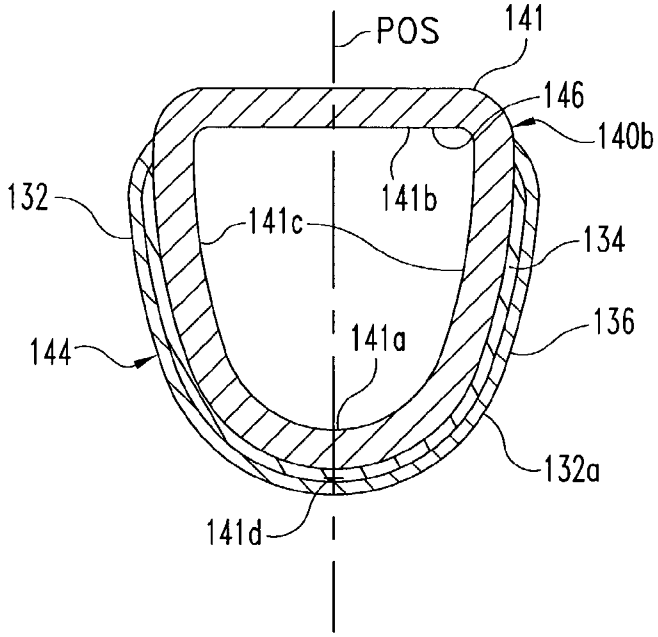
FIG. 9 is a partial, sectional view of the BTE device of FIG. 7 taken along section line 9-9 of FIG. 7.
Figure 11:
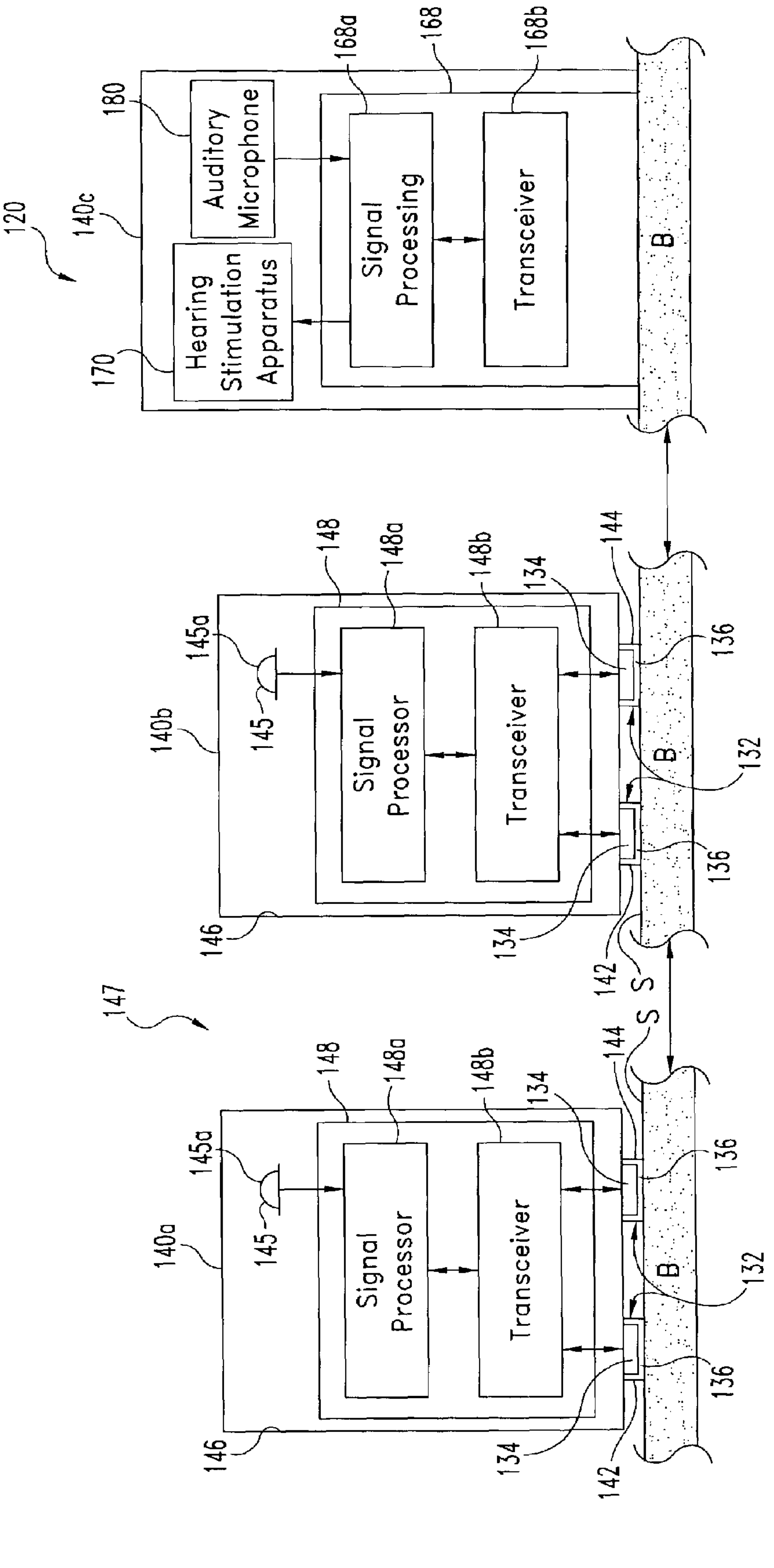
FIG. 11 is a schematic diagram of the system of FIG. 6.

Electrodes 132 are each comprised of a metallic member 134 and a dielectric layer 136 at least partially covering the metallic member 134 as best shown in FIGS. 8, 9, and 11. The composition of members 134 and/or layer 136 can be as described in connection with member 34 and dielectric layer 36 of electrodes 32. For devices 140*a* and 140*b*, each of the upper electrodes 132 are alternatively designated antenna constituent 142, and each of the lower electrodes 132 are alternatively designated antenna constituent 144. Antenna constituents 142 and 144 are operable as a dipole antenna in the near field as alternatively designated by reference numeral 132*a* in FIGS. 8 and 9. In one embodiment, antenna constituent 142 was provided in the form of a 9 millimeter wide copper strip and antenna constituent 144 was provided in the form of a 15 millimeter wide copper strip both having a thickness of 90 micrometers. In other embodiments, a different composition, size, and/or shape of antenna constituents 142, 144 and/or dielectric layer 136 can be utilized as would occur to those skilled in the art.

Housing 141 is generally symmetric about a plane that intersects contour 141*a*. This plane of symmetry (POS) is perpendicular to the view plane of FIGS. 8-10, being represented by the axis labeled POS. The plane of symmetry is parallel to the view plane of FIG. 7. Referring specifically to the partial sectional view of FIG. 8, antenna constituent 142 extends from lower contour 141*d* (represented by cross-hairs) to either of opposing sides 141*c* to present a U or V shape that wraps around the plane of symmetry represented by axis POS and, like housing 141, is generally symmetric about this plane. Referring specifically to the partial sectional view of FIG. 9, antenna constituent 144 extends from lower contour 141*d* (represented by cross-hairs) to opposing sides 141*c* to present a U or V shape that wraps around the plane of symmetry represented by axis POS and, like housing 141, is generally symmetric about this plane. The symmetry of housing 141, antenna constituent 142 and antenna constituent 144 with respect to the plane represented in FIGS. 8 and 9 facilitates the interchangeability of devices 140*a* and 140*b* between right and left ears E1 and E2, respectively.

In one preferred embodiment of devices 140*a* and 140*b*, antenna constituents 142 and 144 are separated from one another along contour 141*d* by at least 10 millimeters to reduce capacitance therebetween. In a more preferred embodiment, the separation distance between antenna constituent 142 and 144 along contour 141*d* of housing 141 is at least 15 millimeters. In a still more preferred embodiment, this separation distance is at least 20 millimeters. Alternatively or additionally, antenna constituent 142 and 144 are arranged along housing 141 so that antenna constituent 142 contacts or is in close proximity to skin region 126*a* above an uppermost extreme 129*a* of concha C of the ear and antenna constituent 144 contacts or is in close proximity to skin region 126*b* at a level below extreme 129*a* as illustrated in FIG. 7. Correspondingly, antenna constituent 142 contacts or is proximal to skin region 126*a* at a point above and anterior to skin region 126*b* as positioned relative to antenna constituent 144. Antenna constituent 142 and 144 can contact or be proximal to skin S that joins the pinnae P1, P2 and corresponding cranial regions CR1, CR2; skin S on the pinnae P1, P2; and/or skin on cranial regions CR1, CR2; respectively.

Figure 10:
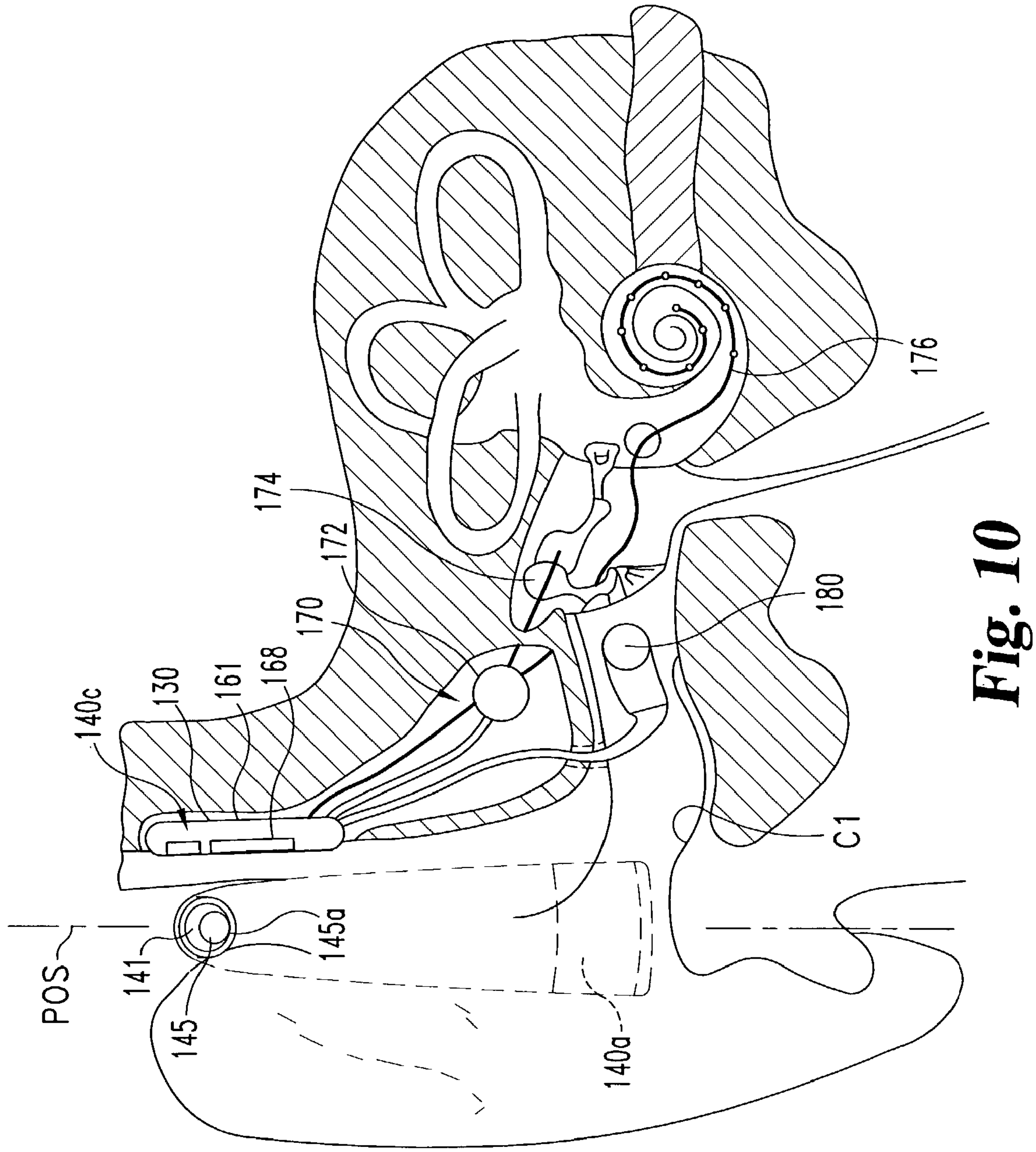
FIG. 10 is a diagrammatic view of the BTE device and cochlear implant of the system of FIG. 6 relative to various structures of the user's right ear shown in partial section.

Referring to FIGS. 10 and 11, each device 140*a* and 140*b* includes a sound sensor 145 in the form of microphone 145*a* that can be any of the types previously described. Collectively, sensors 145 of devices 140*a* and 140*b* define a sound sensing array 147. Housing 141 defines cavity 146 to contain circuitry 148. Circuitry 148 includes transceiver 148*b* coupled to corresponding antenna constituents 142 and 144. Transceiver 148*b* is of the type described in connection with system 20. Circuitry 148 also includes signal processor 148*a* that can be configured in any of the ways described for signal processor 48*a,* with its programmed and/or hardwired logic adapted to perform operations described hereinafter for system 120. Circuitry 148 further includes any power supplies (not shown), filters, signal conditioners, format converters (such as analog-to-digital and/or digital-to-analog converters), volatile memories, nonvolatile memories, and the like desired to perform its operations. Electrical power can be provided in the form of an electrochemical cell or battery and/or a different source as would occur to those skilled in the art.

Implant 140*c* is illustrated in FIG. 10 relative to various internal structures associated with ear E1 and in an operational schematic form in the diagram of FIG. 11. Implant 140*c* includes enclosure 161 encapsulating signal processing circuitry 168. Enclosure 161 is implanted in the mastoid region of ear E1. In one form, enclosure 161 is made from titanium, a ceramic material, or such other body-compatible material as would occur to those skilled in the art. Signal processing circuitry includes signal processor 168*a* and transceiver 168*b*. Implant 140*c* also includes hearing stimulation apparatus 170 coupled to signal processing circuitry 168 via one or more wires or cables from enclosure 161. Hearing stimulation apparatus 170 includes middle ear actuator 172 coupled to the middle ear region in the vicinity of the auditory canal. Hearing stimulation apparatus 170 also includes an electromechanical intracochlear actuator 174, such as a bone conduction cochlear stimulator coupled to the small bones of the ear (malleus, incus, and/or stapes), and intracochlear stimulation electrodes 176 implanted within the cochlea. It should be understood that more or fewer hearing stimulation apparatus, or perhaps only one of these hearing stimulators could be used in other embodiments. Implant 140*c* further includes auditory canal microphone 180 coupled to circuitry 168 via cabling. Microphone 180 can be used to detect acoustic signals in addition to or in lieu of sensors 145 to enhance natural sound perception of the user.

Referring to FIGS. 6-11, certain operational aspects of system 120 are next described. Devices 140*a* and 140*b* are arranged to pick up sound with array 147 and bidirectionally communicate using body B as an electrical signal transmission line between corresponding pairs of antenna constituents 142 and 144 in the manner previously described for the devices 40*a* and 40*b* of system 20. Likewise, one or more of signal processors 148*a* of devices 140*a* and 140*b* can be configured to generate an output in accordance with a fixed or adaptive beamforming routine and/or other binaural signal processing routine. However, instead of or in addition to an earphone (not shown), implant 140*c* receives the output from device 140*a* and/or 140*b* to correspondingly stimulate hearing of the user U with one or more of the hearing stimulation apparatus 170 previously described. Bidirectional communication between devices 140*a* and 140*b,* and implant 140*c* is represented by double-headed arrows in FIG. 11.

Communication between implant 140*c* and one or more of devices 140*a* and 140*b* can be by a wire or cable connection, through magnetic induction with an induction coil, through electrical signal transmission utilizing electrodes of the type provided for communication between devices 140*a* and 140*b,* through ultrasonic communication, and/or through such different means as would occur to those skilled in the art. In one embodiment, implant 140*c* is only configured to receive communication signals. Alternatively or additionally, one or more of devices 140*a* and 140*b* can be arranged to only transmit or receive signals via electrodes 32.

In alternative embodiments, implant 140*c* is provided in a hearing system with one or more ITE and/or CIC hearing system devices that communicate via electrode pairs. For such alternatives, microphone 180 is typically absent. One or more ITE or CIC hearing system devices in these arrangements can be used in addition to or in place of corresponding BTE hearing system devices.

Figure 12:
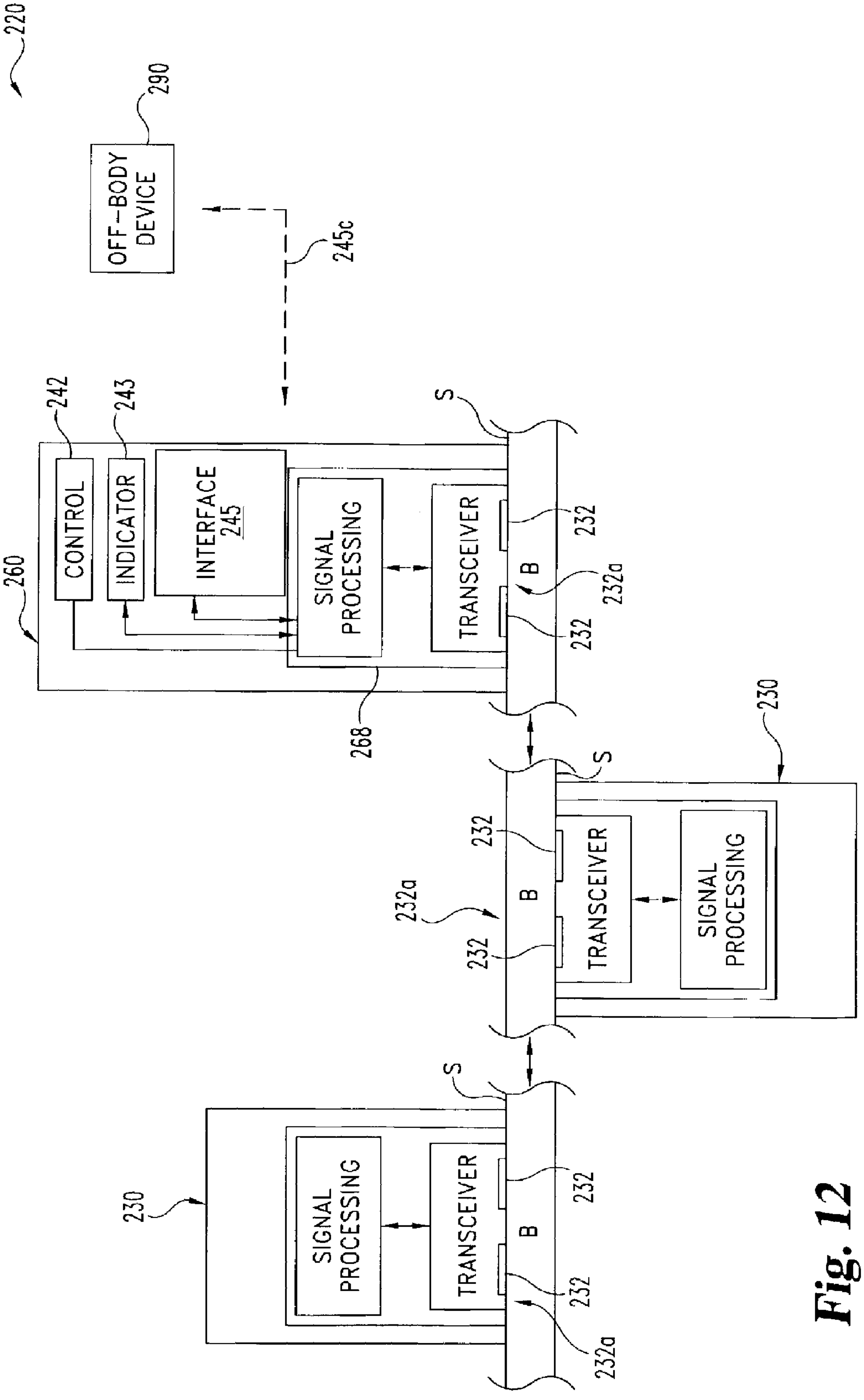
FIG. 12 is a schematic diagram of yet another hearing system.

As an addition or alternative to one or more ITE devices, CIC devices, BTE devices, and implants, a body-worn control device can be utilized. FIG. 12 schematically illustrates communication system 220 including ear-worn hearing system devices 230 each coupled to skin S of body B by a pair of electrodes 232. Devices 230 can be configured the same as ITE devices 40*a* and 40*b,* BTE devices 140*a* and 140*b,* or a combination of these. Correspondingly, electrodes 232 are configured the same as electrodes 32 or 132, and each pairing of electrodes 232 for a device is alternatively designated dipole antenna 232*a*. System 220 further includes hearing system control device 240 with a corresponding electrode pair 232.

Figure 13:
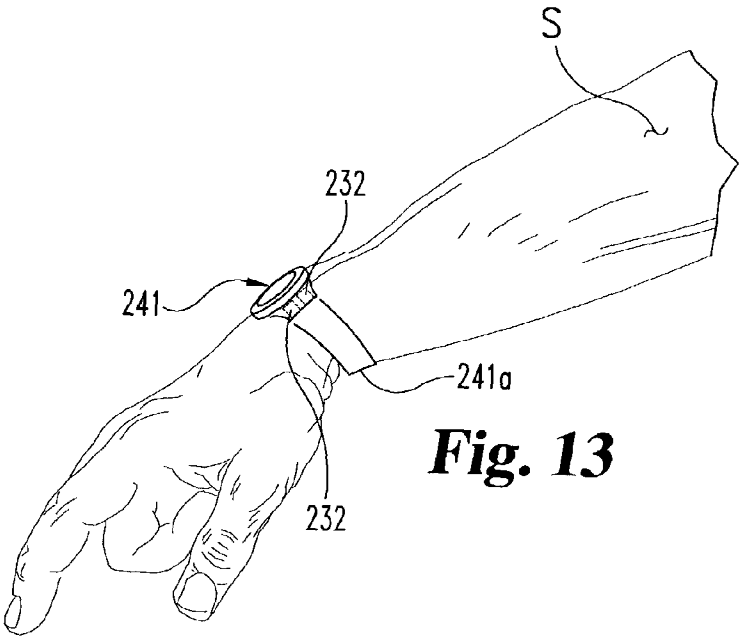
FIG. 13 is a partial diagrammatic view of a first type of hearing system control device as worn by a user.

Device 240 provides user control over system 220 and an off-body communication interface with off-body device 290. Device 240 can be provided in different forms, including but not limited to eyeglasses, a headband, a necklace and the like; or in the form of a wrist worn device 241 with a coupling wrist band or strap 241*a* as shown in FIG. 13. Indeed, device 240 can be integrated into a wristwatch or made to appear as one. The WATCHPILOT provided by PHONAK AG, which has a business address of Laubisrütistrasse 28, 8712 Stäfa, Switzerland, could be adapted to such use. Device 240 includes user control 242 arranged to provide input through one or more push buttons, rotary dials, switches, or the like. Device 240 also includes indicator 243 to provide user-observable output. Indicator 243 is typically in the form of a Liquid Crystal Display (LCD) or Light Emitting Diode (LED) display, but can be differently configured as would occur to those skilled in the art. Device 240 also includes off-body communication interface 245, which can be of a cable connected variety, wireless variety, or a combination of such varieties. In one wireless Radio Frequency (RF) based form, communication is performed in accordance with a BLUETOOTH or AUTOCOM standard, and/or a MICROLINK or MLX standard from PHONAK AG. In addition or as an alternative, interface 245 can communicate through another wireless technique and/or by cable connection.

Device 240 further includes signal processing/communication circuitry 268 coupled to control 242, indicator 243, and interface 245. In one nonlimiting form, circuitry 268 includes one or more signal processing units operable to execute programmed and/or hardwired logic to facilitate Input and/or Output (I/O) via control 242, indicator 243, interface 245, and perform any desired data modifications, conversions, storage, or the like; and includes any signal conditioners, filters, format converters (such as analog-to-digital and/or digital-to-analog types), amplifiers, power sources, or the like to implement desired operations as would occur to those skilled in the art. Device 240 communicates with devices 230 through a time-varying electrical signal transmitted through body B via electrodes 232 in the manner previously described in connection with systems 20 and 120.

Interface 245 operatively connects with off-body device 290 via a communication link represented by the doubled headed arrow designated with reference numeral 245*c*. This communication link can be of a temporary or relatively permanent type. Off-body device 290 can be arranged as an audio satellite, providing a remote audio input to the user from a Public Address System (PAS), telephonic communication link, one or more remote microphones, an entertainment source such as a radio, television, MP3 player, tape player, CD player, etc. and/or a different type of audio satellite as would occur to those skilled in the art, just to name a few. Alternatively or additionally, off-body device 290 can provide data and/or parametric values used in the operation of system 220. Interface 245 can also be used in conjunction with device 290 to perform testing of one or more devices 230 and/or of system 220 collectively; communicate system or device diagnosis; and/or system/device performance data.

Figure 14:
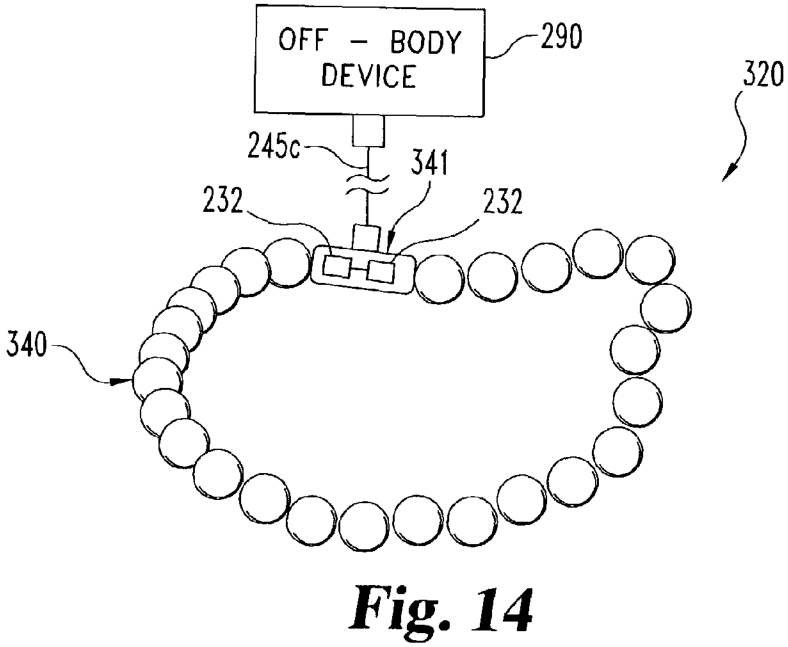
FIG. 14 is a partial diagrammatic view of a second type of hearing system control device.

FIG. 14 depicts a partial diagrammatic view of communication system 320, where like reference numerals refer to like features. System 320 can include one or more of the ear worn devices of systems 20, 120, and 220 and/or one or more implants 140*c* (not shown) that communicate with time-varying electrical signals transmitted through body B. System 320 includes an alternative body-worn control device in the form of jewelry that is depicted as bracelet 340 with control device 341. Bracelet 340 is shown interfaced with off-body device 290, and includes electrodes 232. Control device 341 can incorporate the features of device 240. In another embodiment of a control device with the appearance of jewelry, an earring is utilized that clips to an earlobe of the user. In further embodiments, two or more control devices can be utilized and/or one or more implants may also be included. Additionally or alternatively, a control device can be used in lieu of one or more ear-worn modules, such as ITE, CIC, or BTE devices. In still other embodiments, a control device is not worn or carried on the body, but instead is temporarily used to provide audio input, perform diagnostic testing, update/modify software, or perform such different operation as would occur to those skilled in the art.

As in the case of system 20, ear-to-ear communication can be utilized between BTE devices 140*a* and 140*b* of system 120 to implement a fixed or adaptive beamformer routine or a different binaural routine. In still another embodiment, at least one of BTE devices 140*a* and 140*b* is configured with an earphone to stimulate hearing of user U with adaptation to operate in the manner described for devices 40*a* and 40*b* of system 20, and implant 140*c* being absent. System 420 depicted in FIG. 15 provides an example of a BTE device 440 with earphone 447*a*.

Figure 15:
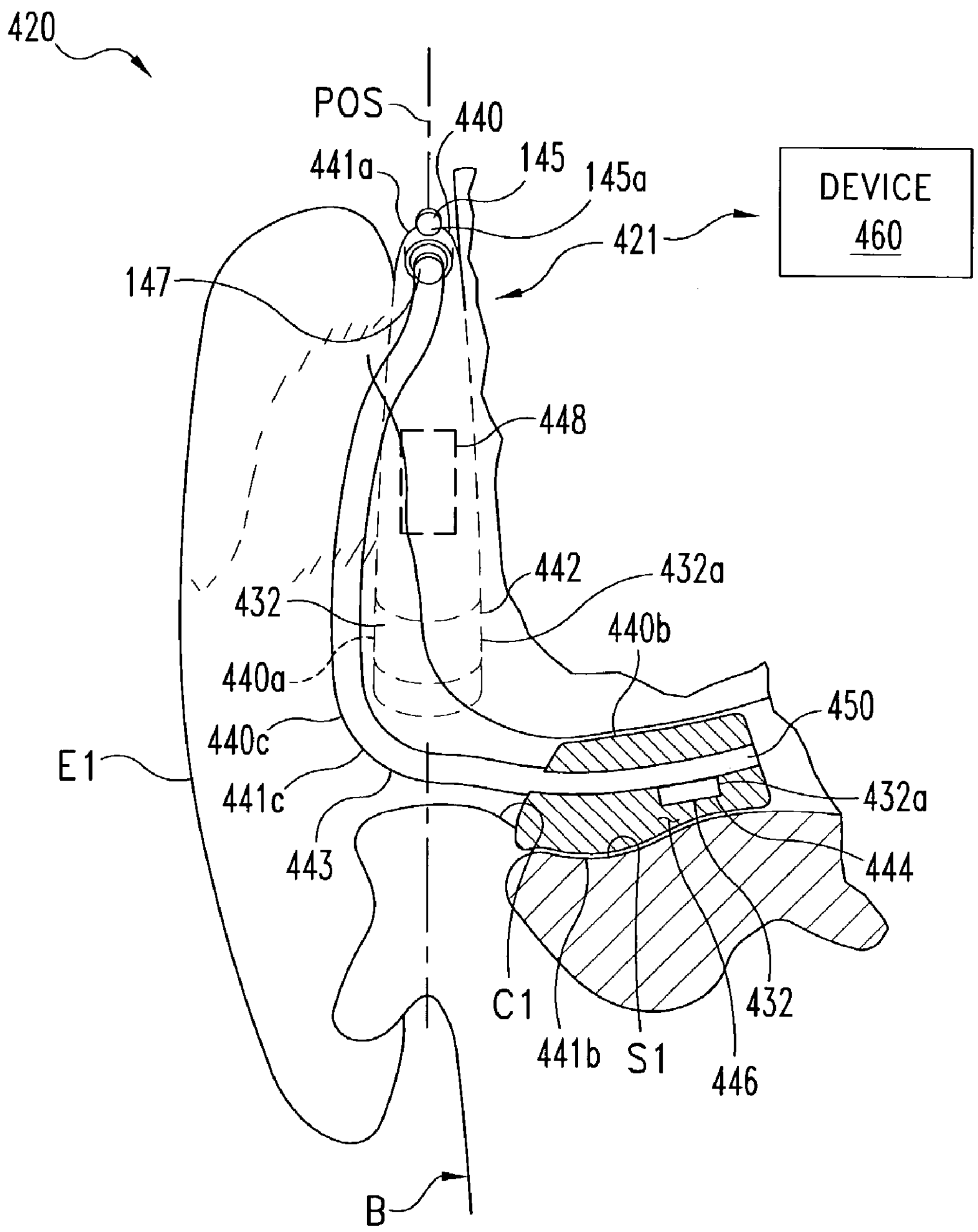
FIG. 15 is a partial schematic view of still another hearing system.

FIG. 15 illustrates still another communication system 420 where like reference numerals refer to like features previously described. System 420 is in the form of hearing system 421 that includes hearing system devices 440 and 460. Hearing system device 440 includes member 440*a* coupled to member 440*b* by member 440*c*. Member 440*a* includes a rigid housing member 441*a* shaped and configured to fit behind the ear E1 of a person's body B. Housing member 441*a* can be shaped the same as housing 141 of devices 140*a* and 140*b* described in connection with system 121. Member 440*a* also includes sensor 145 in the form of microphone 145*a* as previously described, and a hearing stimulator 447 that can be of the type described in connection with devices 40*a* and 40*b* of system 20. Sensor 145 is immediately above stimulator 447. Further, member 440*a* houses circuitry 448 that is configured the same as circuitry 48, 148, and/or variations thereof to perform fixed beamforming, adaptive beamforming, and/or different binaural routines with adaptation to include logic to operate device 440 according to the manner described hereinafter. Circuitry 448 is operatively coupled to sensor 145 and hearing stimulator 447.

Member 440*b* is in partial schematic, sectional form in FIG. 15. Member 440*b* includes housing member 441*b* shaped to fit in ear canal C1 in the manner described in connection with device 40*a* of system 20. Member 440*b* defines passageway 450 to transmit sound to ear E1 received from member 440*c*. Member 440*c* includes flexible housing 441*c* in the form of coupling tube 443 with a passage to transmit this sound from hearing stimulator 447 of member 440*a* to passageway 450 of member 440*b*. Housing 441*c* is flexible to permit articulation of members 440*a* and 440*b* relative to one another such that member 440*b* can be readily removed from and inserted in canal C1 while member 440*a* is mounted behind ear E1.

Device 440 includes a pair of electrodes 432 configured to provide a dipole antenna designated by reference numeral 432*a*. Electrode 432 carried with member 440*a* is alternatively designated antenna constituent 442, and electrode 442 carried with member 440*b* is alternatively designated antenna constituent 444. Further, antenna constituent 444 is shown embedded within member 440*b* such that portion 446 of member 440*b* is positioned between skin S1 along ear canal C1 and antenna constituent 444. Portion 446 is comprised of a dielectric material to facilitate capacitive coupling of antenna constituent 444 to body B. Electrodes 432 are composed of a metallic material or other suitable electrical conductor. Electrodes 432 are each operatively coupled to circuitry 448. In the case of antenna constituent 444, coupling to circuitry 448 can be accomplished by a cable or wire (not shown) that extends through or is carried with housing member 441*c*.

System 421 can operate in the same manner as system 21 to enhance normal hearing and/or impaired hearing. Device 460 can be another device 440; device 40*b*, 140*a*, or 140*b*; or another of the various hearing systems devices previously described, such as a CIC, control device (with or without an off-body interface), and/or implant, to name just a few. Communication between device 440 and 460 can be performed in the same manner as described for previous devices via electrode pairs with each pair operating as a dipole antenna in close proximity to or contact with body B.

Figure 16:
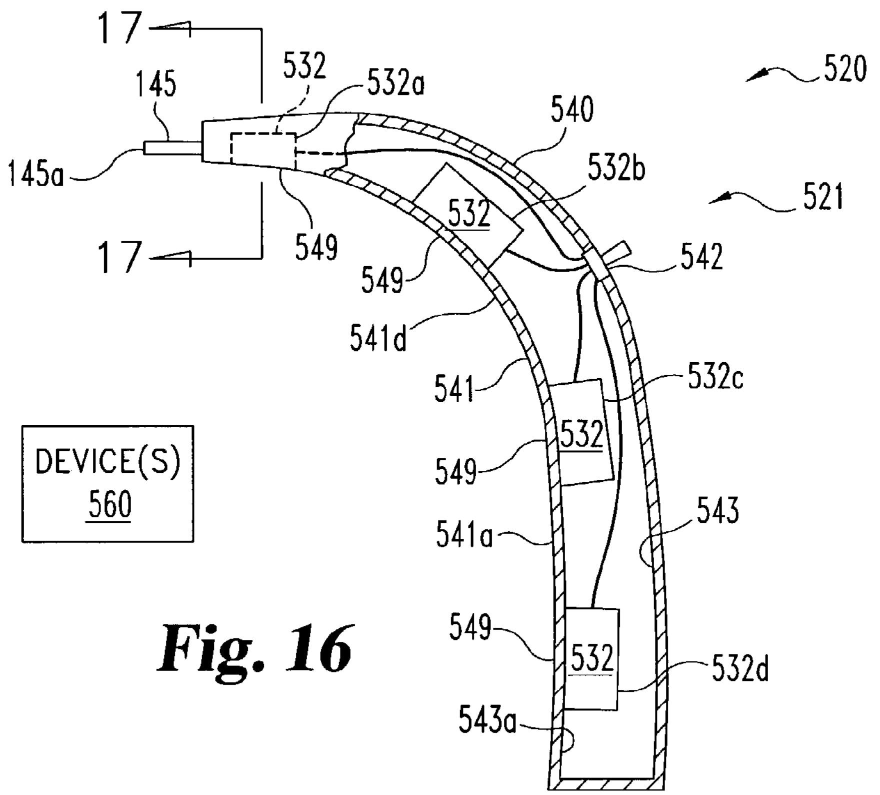
FIG. 16 is a side view of a BTE device of a further hearing system.
Figure 17:
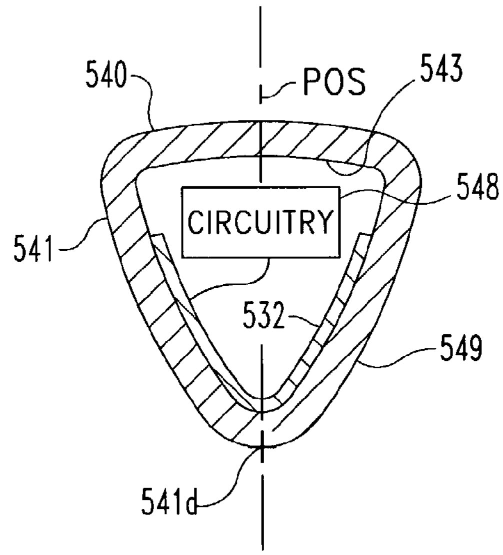
FIG. 17 is a partial, sectional view of the BTE device of FIG. 16.

FIGS. 16 and 17 illustrate yet another communication system 520. System 520 includes hearing system device 540 in the form of a behind-the-ear unit and other hearing system device(s) 560. Device 540 includes housing 541 that can be shaped the same as housing 141 of device 140*a* or 140*b* previously described. Device 540 further includes a number of internal electrodes 532 (four of which are shown). Electrodes 532 are carried within interior 543 of device 540 and are operatively coupled to user control 542. Device 540 also includes user control 542 coupled to electrodes 532. In one form, control 542 is a momentary push-button that can be used to provide an input pulse. Device 540 also includes sensor 145 in the form of microphone 145*a* as previously described.

Electrodes 532 are separated from outer surface 541*a* of housing 541 along lowermost contour 541*d* by portions 549 of housing 541. Electrodes 532 are positioned to contact interior surface 543*a* of housing 541, and have more specific individual designations 532*a*, 532*b*, 532*c*, and 532*d*. In one form, electrodes 532 are plated or otherwise deposited on surface 543*a* using standard techniques, and are comprised of a metallic material or other suitable electrical conductor. Portions 549 are comprised of a dielectric material configured to capacitively couple electrodes 532 to skin when device 540 is worn behind the ear of a user.

The partial sectional view of FIG. 17 schematically illustrates circuitry 548 of device 540 that is carried in interior 543 of housing 541. Circuitry 548 can be configured the same as previously described circuitry 48, 148, and/or variations thereof to perform fixed beamforming, adaptive beamforming, and/or a different binaural routine with the exception of adaptations to include logic to operate device 540 according to the manner described hereinafter. Circuitry 548 is operatively coupled to electrodes 532, control 542, and sensor 145. With circuitry 548, any pair of electrodes 532 can be utilized as a dipole antenna to communicate through the body of a user in the manner previously described.

FIG. 17 also shows a representative cross-section of one of electrodes 532 illustrating its symmetry about axis POS; where axis POS is coextensive with a plane of symmetry for housing 541 and electrodes 532 to facilitate interchange of device 540 between right and left ears.

In operation, circuitry 548 responds to an input from control 542, to successively cause different pairs of electrodes 532 to become active and correspondingly form a dipole antenna. Accordingly, an operator of device 540 can select between different pairings of electrodes 532 to find which electrode pair operates best for communication purposes with one or more of other device(s) 560 (FIG. 16). In an example in which control 542 is a momentary pushbutton type, each time the pushbutton is depressed by an operator, a corresponding electrical signal is generated. Circuitry 548 of device 540 responds to this signal to activate a different one of a number of pairings of electrodes 532. A typical initial pair includes electrodes 532 separated from one another by the greatest distance, specifically electrodes 532*a* and 532*d*. Other pairings selectable with control 542 include: electrodes 532*a* and 532*c*; electrodes 532*a* and 532*b*; electrodes 532*b* and 532*c*; electrodes 532*b* and 532*d*; and electrodes 532*c* and 532*d*.

In other embodiments, not all of the possible unique pairings are offered as an option and the technique to switch from one to the next may differ. Alternatively or additionally, selection can be done with a different type of control and/or can be done in response to programming or another automatic procedure. In one example, the pairing is selected via an off-body unit. When a given electrode pair is active, the remaining electrodes are not typically utilized to perform communications—being in an inactive state. Naturally, in other embodiments more or fewer electrodes could be utilized than the four illustrated in FIG. 16. For further embodiments, different active pairings can be selected among possible pairings of three or more electrodes; where some or all of these electrodes are exterior to the device housing and may or may not otherwise include a dielectric covering. Likewise, electrode pairing selection for devices having three or more electrodes could be utilized with ITC devices, CIC devices, control devices, and the like for other hearing system configurations of the type described herein, or as would otherwise occur to those skilled in the art. Further, it is envisioned that alternative pairings of electrodes for intrabody communication systems and networks other than those used to enhance normal hearing or impaired hearing could be utilized.

It should be understood that in alternative embodiments any of the communication techniques and arrangements of the present application could be utilized for systems other than those directed to enhancement of normal or impaired hearing. For example, user controlled computing devices such as Personal Digital Assistants (PDAs) could be coupled to an intrabody network with a corresponding electrode pair operating as dipole antennae. Alternatively or additionally, medical diagnostic and/or treatment devices could communicate in such a fashion. Also, mobile phones, microphones, headphones, virtual reality devices and various other units that may or may not involve hearing and sound reception could utilize dipole antenna communication via electrode pairs of any of types described in connection with the systems 20, 120, 220, 320, 420, and 520 to participate in a body area network.

All publications, patents, and patent applications cited in this specification are herein incorporated by reference as if each individual publication, patent, or patent application were specifically and individually indicated to be incorporated by reference and set forth in its entirety herein. Further, any theory, mechanism of operation, proof, or finding stated herein is meant to further enhance understanding of the present invention and is not intended to make the present invention in any way dependent upon such theory, mechanism of operation, proof, or finding. While the invention has been illustrated and described in detail in the drawings and foregoing description, the same is to be considered as illustrative and not restrictive in character, it being understood that only selected embodiments have been shown and described and that all changes, modifications and equivalents that come within the spirit of the invention as defined herein and/or by the following claims are desired to be protected.

What is claimed is:

1. Apparatus, comprising:

a first hearing system device including a housing structured for removal and placement by a person through an outer ear canal of the person, circuitry included within the housing, and two electrodes each electrically coupled to the circuitry; and wherein the housing includes a first side portion positioned opposite a second side portion, a first one of the electrodes is connected to the first side portion to be positioned along a first skin region of the ear canal, a second one of the electrodes is connected to the second side portion of the housing to be positioned along a second skin region of the ear canal opposite the first skin region, the electrodes each include a metallic member and a dielectric layer covering at least a portion of the metallic member, the dielectric layer being selected to make skin contact, and the electrodes and the circuitry are operable to selectively communicate information through the person when the housing is received in the ear canal.

2. The apparatus of claim 1, wherein the electrodes are structured to collectively operate as a dipole antenna.

3. The apparatus of claim 1, further comprising an implant operable to receive the information from the first hearing system device.

4. An apparatus, comprising:

a first hearing system device including a housing structured for removal and placement by a person through an outer ear canal of the person, circuitry included within the housing, and two electrodes each electrically coupled to the circuitry;

wherein the housing includes a first side portion positioned opposite a second side portion, a first one of the electrodes is connected to the first side portion to be positioned along a first skin region of the ear canal, a second one of the electrodes is connected to the second side portion of the housing to be positioned along a second skin region of the ear canal opposite the first skin region, and the electrodes and the circuitry are operable to selectively communicate information through the person when the housing is received in the ear canal; and a second hearing system device carrying two other electrodes to communicate electrical signals through skin of the person, the second hearing system device including means for communicating with the first hearing system device through the other electrodes.

5. The apparatus of claim 4, wherein the second hearing system device is shaped to be received in another ear canal of the person.

6. The apparatus of claim 4, further comprising a third hearing system device operable to selectively communicate with at least one of the first hearing system device and the second hearing system device utilizing at least a portion of the person as a transmission line.

7. The apparatus of claim 4, wherein the first hearing system device and the second hearing system device are operable to bidirectionally communicate through the person when the electrodes of the first hearing system device and the other electrodes of the second hearing system device are placed proximate to or in contact with the person's skin.

8. The apparatus of claim 7, further comprising a hearing system control device with a corresponding electrode pair to communicate with at least one of the first hearing system device and the second hearing system device.

9. The apparatus of claim 8, further comprising an off-body device effective to selectively communicate with the hearing system control device.

10. The apparatus of claim 1, wherein the first one of the electrodes is positioned along the housing to contact the first skin region along a top portion of the ear canal and the second one of the electrodes is positioned along the housing to contact the second skin region along a bottom portion of the ear canal.

11. Apparatus, comprising:

a first hearing system device including a housing, circuitry included within the housing, and a pair of electrodes each coupled to the circuitry to communicate information through a person; and wherein the housing defines a lower, hook-shaped contour to fit behind an ear of the person and be placed along the person's skin between a corresponding pinna and cranial region, the electrodes are each positioned along the contour and spaced apart from one another by at least about 10 millimeters to be placed proximate to a corresponding pair of skin regions when the device is mounted behind the ear of the person.

12. The apparatus of claim 11, wherein the electrodes each include a metallic member and a dielectric layer covering at least a portion of the metallic member, the dielectric layer of each of the electrodes being selected to contact a corresponding one of the skin regions.

13. The apparatus of claim 11, wherein the electrodes are structured to collectively provide a dipole antenna.

14. The apparatus of claim 11, wherein the housing includes a first side opposite a second side and the electrodes each extend to the first side and the second side from the contour.

15. The apparatus of claim 14, wherein the electrodes are generally symmetric about a plane intersecting the contour, the device being interchangeable between the right and left ears.

16. The apparatus of claim 11, wherein a first one of the electrodes is located along the device to contact a first one of the skin regions positioned at least as high as an uppermost extreme of the concha and anterior to a second one of the skin regions, the second one of the skin regions is positioned below the uppermost extreme, and a second one of the electrodes is located along the device to contact the second one of the skin regions when the device is mounted behind the ear of the person.

17. The apparatus of claim 16, wherein the electrodes are separated from one another along the contour by at least 15 millimeters.

18. The apparatus of claim 11, further comprising a second hearing system device shaped to fit behind another ear of the person, the second hearing system device including another pair of electrodes to be positioned along a corresponding pair of skin regions of the person to communicate through the person with the first hearing system device.

19. The apparatus of claim 18, further comprising a third hearing system device effective to communicate with at least one of the first hearing system device and the second hearing system device, the third hearing system device being one of a control device and an implant.

20. The apparatus of claim 19, wherein the third hearing system device is the control device and further comprising an off-body device operable to selectively communicate with the control device.

21. Apparatus, comprising:

a first hearing system device including a housing, circuitry included within the housing, and a pair of electrodes each coupled to the circuitry to communicate information through a person; and wherein the housing includes a first side opposite a second side, the first side and second side are connected together by a lower portion defining a hook-shaped contour to fit behind an ear of the person, the electrodes each extend from the contour to the first side and the second side, and the electrodes are each approximately symmetric about a plane intersecting the contour, and the first hearing system device is interchangeable between the right and left ears.

22. The apparatus of claim 21, wherein the electrodes each include a metallic member and a dielectric layer covering at least a portion of the metallic member, the dielectric layer being selected to make skin contact.

23. The apparatus of claim 21, wherein the electrodes are structured to collectively operate as a dipole antenna proximate to or in contact with a respective pair of skin regions.

24. The apparatus of claim 21, further comprising a second hearing system device shaped to fit behind another ear of the person, the second hearing system device including means for communicating with the first hearing system device.

25. The apparatus of claim 24, further comprising a third hearing system device effective to communicate with at least one of the first hearing system device and the second hearing system device, the third hearing system device being one of a control device and an implant.

26. The apparatus of claim 25, wherein the third hearing system device is the control device and further comprising an off-body device operable to selectively communicate with the control device.

27. A behind-the-ear device, comprising: a housing, circuitry included within the housing, and a pair of electrodes each coupled to the circuitry to communicate information through a person, the housing including an inner contour shaped to fit behind an ear of the person between a corresponding pinna and cranial region, the electrodes being positioned along the inner contour and spaced apart from one another by at least about 10 millimeters to be positioned along a respective pair of spaced-apart skin regions when the device is mounted behind the ear of the person.

28. The device of claim 27, wherein the electrodes collectively operate as a dipole antenna.

29. The device of claim 27, wherein one or more of the electrodes are formed along an interior surface of the housing, and one or more corresponding portions of the housing are comprised of a dielectric selected for placement in close proximity to or in contact with the person's skin.

30. The device of claim 27, further comprising another pair of electrodes spaced apart from one another along the housing and a control to select among different active pairings of the electrodes.

31. A device for placement in an ear canal of a person, comprising: a housing shape structured for removal and placement through an outer ear canal by the person, circuitry included within the housing, a first electrode electrically coupled to the circuitry and being carried with the housing to be placed along a first skin region at a top portion of the ear canal, and a second electrode electrically coupled to the circuitry and being carried with the housing to be placed along a second skin region at a bottom portion of the ear canal, the first electrode and the second electrode being structured to collectively operate as a dipole antenna, and the first electrode, the second electrode, and the circuitry being effective to selectively communicate information through the person when the housing is received in the ear canal of the person.

32. A behind-the-ear device comprising: a housing, circuitry included within the housing, and a pair of electrodes each coupled to the circuitry to communicate information through a person; and wherein the housing includes a first side opposite a second side, the first side and second side are connected together by a lower portion defining a hook-shaped contour to fit behind an ear of the person, the electrodes each wrap about a plane intersecting the contour and extend from the contour to the first side and the second side.

33. The device of claim 32, wherein the electrodes are each approximately symmetric about the plane, are spaced apart from one another by at least 10 millimeters along the contour, and collectively operate as a dipole antenna.

34. The device of claim 32, wherein the first electrode and second electrode are each formed along an interior surface of the housing with one or more corresponding portions of the housing being comprised of a dielectric material selected for placement in close proximity to or in contact with the person's skin.

35. The device of claim 32, further comprising a third electrode positioned along the housing and a control to select among different active pairings of the first electrode, the second electrode, and the third electrode.

36. Apparatus, comprising:

a first hearing system device including a housing structured for removal and placement by a person through an outer ear canal of the person, circuitry included within the housing, and two electrodes each electrically coupled to the circuitry;

an implant operable to receive the information from the first hearing system device; and wherein the housing includes a first side portion positioned opposite a second side portion, a first one of the electrodes is connected to the first side portion to be positioned along a first skin region of the ear canal, a second one of the electrodes is connected to the second side portion of the housing to be positioned along a second skin region of the ear canal opposite the first skin region, and the electrodes and the circuitry are operable to selectively communicate information through the person when the housing is received in the ear canal.

37. The apparatus of claim 36, further comprising a second hearing system device carrying two other electrodes to communicate electrical signals through skin of the person with the first hearing system device.

38. The apparatus of claim 37, further comprising a third hearing system device operable to selectively communicate with at least one of the first hearing system device and the second hearing system device utilizing at least a portion of the person as a transmission line.

39. The apparatus of claim 37, wherein the first hearing system device and the second hearing system device are operable to bidirectionally communicate through the person when the electrodes of the first hearing system device and the other electrodes of the second hearing system device are placed proximate to or in contact with the person's skin.

40. Apparatus, comprising:

a first hearing system device including a housing structured for removal and placement by a person through an outer ear canal of the person, circuitry included within the housing, and two electrodes each electrically coupled to the circuitry; and wherein the housing includes a first side portion positioned opposite a second side portion, a first one of the electrodes is connected to the first side portion to be positioned along a first skin region of the ear canal, a second one of the electrodes is connected to the second side portion of the housing to be positioned along a second skin region of the ear canal opposite the first skin region, the first one of the electrodes is positioned along the housing to contact the first skin region along a top portion of the ear canal and the second one of the electrodes is positioned along the housing to contact the second skin region along a bottom portion of the ear canal, and the electrodes and the circuitry are operable to selectively communicate information through the person when the housing is received in the ear canal.

41. The apparatus of claim 40, further comprising a second hearing system device carrying two other electrodes to communicate electrical signals through skin of the person with the first hearing system device.

42. The apparatus of claim 41, wherein the first hearing system device and the second hearing system device are operable to bidirectionally communicate through the person when the electrodes of the first hearing system device and the other electrodes of the second hearing system device are placed proximate to or in contact with the person's skin.

43. The apparatus of claim 40, further comprising an implant operable to receive the information from the first hearing system device.

* * * * *